United States Patent
Crawley et al.

(10) Patent No.: US 7,178,378 B2
(45) Date of Patent: Feb. 20, 2007

(54) RESONANT SENSOR AND SENSING SYSTEM

(75) Inventors: Ed Crawley, Cambridge, MA (US);
Mark Lundstrom, Boston, MA (US);
Brett Masters, Belmont, MA (US);
Alok Srivastava, Alston, MA (US);
Martin Schmidt, Reading, MA (US);
Michael Miller, Hollis, NH (US)

(73) Assignee: BioScale, Inc., Cambridge, MA (US)

( * ) Notice: Subject to any disclaimer, the term of this patent is extended or adjusted under 35 U.S.C. 154(b) by 111 days.

(21) Appl. No.: 10/651,338

(22) Filed: Aug. 28, 2003

(65) Prior Publication Data

US 2005/0005676 A1    Jan. 13, 2005

Related U.S. Application Data

(60) Provisional application No. 60/406,808, filed on Aug. 29, 2002.

(51) Int. Cl.
*G01N 23/036* (2006.01)

(52) U.S. Cl. ............ 73/24.06; 73/24.01; 73/64.53

(58) Field of Classification Search ........ 73/24.01, 73/24.06, 64.53
See application file for complete search history.

(56) References Cited

U.S. PATENT DOCUMENTS

| | | |
|---|---|---|
| 4,752,855 A | 6/1988 | Fedter et al. |
| 4,920,450 A | 4/1990 | Masiulis |
| 5,025,346 A | 6/1991 | Tang et al. |
| 5,079,600 A | 1/1992 | Schnur et al. |
| 5,129,262 A | 7/1992 | White et al. |
| 5,189,914 A | 3/1993 | White et al. |
| 5,306,644 A | 4/1994 | Myerholtz et al. |
| 5,411,709 A * | 5/1995 | Furuki et al. ............. 422/91 |
| 5,451,683 A | 9/1995 | Barrett et al. |
| 5,482,867 A | 1/1996 | Barrett et al. |
| 5,512,131 A | 4/1996 | Kumar et al. |
| 5,620,850 A | 4/1997 | Bamdad et al. |
| 5,660,985 A | 8/1997 | Pieken et al. |
| 5,719,324 A * | 2/1998 | Thundat et al. .......... 73/24.01 |
| 5,776,748 A | 7/1998 | Singhvi et al. |
| 5,900,160 A | 5/1999 | Whitesides et al. |
| 6,197,515 B1 | 3/2001 | Bamdad et al. |
| 6,295,861 B1 * | 10/2001 | Tom et al. ............. 73/24.06 |

(Continued)

FOREIGN PATENT DOCUMENTS

WO    WO-02/95099    11/2002

OTHER PUBLICATIONS

"A Stand-alone Acoustic Wave Sensor for Liquid Viscosity Measurement" (English Abstract).

(Continued)

*Primary Examiner*—Hezron Williams
*Assistant Examiner*—Paul M. West
(74) *Attorney, Agent, or Firm*—Proskauer Rose LLP

(57) ABSTRACT

The disclosed sensor chip includes a substrate and a moving member coupled to the substrate and disposed for movement relative to the substrate. The moving member moves relative to the substrate in a first direction and in a second direction in response to movement of the substrate. The first direction is different than the second direction. The moving member includes a plurality of receptors. The receptors are configured for selectively binding to a first measurand.

40 Claims, 14 Drawing Sheets

U.S. PATENT DOCUMENTS

| | | |
|---|---|---|
| 6,322,979 B1 | 11/2001 | Bamdad et al. |
| 6,326,563 B1 | 12/2001 | Takeuchi et al. |
| 6,329,209 B1 | 12/2001 | Wagner et al. |
| 6,365,418 B1 | 4/2002 | Wagner et al. |
| 6,368,838 B1 | 4/2002 | Singhvi et al. |
| 6,368,877 B1 | 4/2002 | Zhang et al. |
| 6,406,921 B1 | 6/2002 | Wagner et al. |
| 6,457,361 B1 | 10/2002 | Takeuchi et al. |
| 6,472,148 B1 | 10/2002 | Bamdad et al. |
| 6,518,168 B1 | 2/2003 | Clem et al. |
| 2002/0042074 A1 | 4/2002 | Bamdad et al. |
| 2002/0094572 A1 | 7/2002 | Singhvi et al. |

OTHER PUBLICATIONS

Balantine et al., "Acoustic Wave Sensors: Theory, Design, and Physico-Chemical Applications," Academic Press, San Diego, 1997.

Berg et al., "Bispecific antibodies that Mediate Killing of Cells Infected with Human Immunodeficiency Virus of any Strain", Proc. Natl. Acad. Sci., USA, 88:4723-4727 (1991).

Chaudhary et al.,"A Rapid Method of Cloning Functional Variable-region Antibody Genes in Escherichia coli as Single Chain Immunotoxins", Proc. Natl. Acad. Sci., USA, 87:1066-1070 (1990).

Collings et al., "Biosensors: Recent Advances", Rep. Prog. Phys., 60:1397-1445 (1997).

Cunningham et al., "Design, Fabrication and Vapor Characterization of a Microfabricated Flexural Plate Resonator Sensor and Application to Integrated Sensor Arrays", Sensors and Actuators B, 73:112-123 (2001).

Ellington et al., "In vitro Selection of RNA Molecules that Bind Specific Ligands," Nature, 346:818-822 (1990).

Gianchandani et al., "A Bulk Silicon Dissolved Wafer Process for Microelectromechanical Devices," J. Mems, 1(2): 77-85 (1992).

Giesler et al., "Electrostatically excited and capacitively detected flexural plate waves on thin silicon nitride membranes with chemical sensor applications," Sensors and Actuators, 18-19:103-106 (1994).

Giesler et al., "Electrostatic excitation and capacitive detection of flexural plate-waves" Sensor and Actuators, 36: 113-119 (1993).

Grate, "Flexural Plate Wave Devices for Chemical Analysis" Anal. Chem., 63(15): 1552-1561 (1991).

Houser et al., "Rational Materials Design of Sorbent Coatings for Explosives: Applications With Chemical Sensors," Talanta, 54: 469-485 (2001).

Huse et al., "Generation of a Large Combinatorial Library of the Immunoglobulin Repertoire in Phage Lambda", Science, 246:1275-1289 (1989).

Iqbal et al., "A review of molecular recognition technologies for detection of biological threat agents," Biosensors & Bioelectronics, 15: 549-578 (2002).

Lyer et al., "Accelerated Hybridization of Oligonucleotides to Duplex DNA", J. Biol. Chem. 270(24):1412-14717 (1995).

Joyce, "Amplification, Mutation and Selection of Catalytic RNA", Gene, 82:83-87 (1989).

Klug et al., "All you wanted to know about SELEX", Mol. Biol. Reports, 20:97-107 (1994).

Luppa et al., "Immunosensors-principles and applications to clinical chemistry," Clinica Chimica Acta, 314: 1-26 (2001).

McGill et al., "Choosing Polymer Coatings for Chemical Sensors," Chemtech, 27-37 (1994).

Moody et al., "Regiospecific inhibition of DNA duplication by antisense phosphate-methylated oligodeoxynucleotides", Nucleic Acids Res., 17:4769-4782 (1989).

Mullinax et al., "Identification of human antibody fragment clones specific for tetanus toxoid in a bacteriophage A immunoexpression library," Proc. Natl. Acad. Sci. USA, 87:8095-8099 (1990).

Nielsen et al., "Sequence-Selective Recognitino of DNA by Strand Displacement with a Thymine-Substituted Polyamide" Science, 254:1497-1500 (1999).

Ortigao et al., "Antisense Effect of Oligodeoxynucleotides with Inverted Terminal Internucleotidic Linkages: A Minimal Modification Protecting against Nucleolytic Degredation," Antisense Res. Devel., 2:129-146 (1992).

Padmanabhan et al., "A Silicon Micromachined Floating-Element Shear-Stress Sensor with Optical Position Sensing by Photodiodes" J. Microelectro Systems, 5(4):307-315 (1996).

Padmanabhan et al., "A wafer-bonded floating-element shear stress microsensor with optical position sensing photodiodes," J. Mems, 5(4) 1996.

Pluckthun, "Antibodies from Escherichia coli," Nature, 347:497-498 (1990).

The Quartz-Crystal Microbalance in Life Science, Angewandte Chemie.

Savran et al., "Fabrication and Characterization of a Micromechanical Sensor for Differential Detection of Nanoscale Motions," J. Microelectro. Systems, 11(6): 703-708 (2002).

Sinha et al., "Polymer support oligonucleotide synthesis XVIII: use of B-cyanoethyl-N, N-dialkylamino-/N-morpholino phosphoramidite of deoxynucleosides for the synthesis of DNA fragments simplifying deprotection and isolation of the final product," Nucleic Acids Res., 12(11): 4539-4557 (1984).

Steinem et al., "Piezoelectric Mass-Sensing Devices as Biosensors - An Alternative to Optical Biosensors?", Agnew. Chem. Int. Ed., 39:4004-4032 (2000).

Tuerk et al., "Systematic Evolution of Ligands by Exponential Enrichment: RNA Ligands to Bacteriophage T4 DNA Polymerase" Science, 249:505-510 (1990).

Weinberg et al., "Modeling Flexural Plate Wave Devices", J. of Microelectromechanical Systems, 9(3):370-379 (2000).

Wenzel, et al., "Analytic Comparison of the Sensitivities of Bulk-Wave, Surface-Wave and Flexural Plate-Wave Ultrasonic Gravimetric Sensors", Appl. Phys. Lett. 54(20): 1976-1978 (1989).

Wetmur,"DNA Probes: Applications of the Principles of Nucleic Acid Hybridization," Crit. Rev. Biochem. Mol. Biol., 26(3/4): 227-259 (1991).

Wong, "Chemistry of Protein Coniugation and Cross-Linking," CRC Press, Boca Raton, Fla., 1993.

Wood et al., "High Level Synthesis of Immunoglobulins in Chinese Hamster Ovary Cells," J. Immunol, 145(9):3011-3016 (1990).

Yaralioglu et al., "Analysis and design of an interdigital cantilever as a displacement sensor," J. Applied Physics, 83(12): 7405-7415 (1998).

Yazdi et al., "Micromachined Inertial Sensors, " Proceedings of the IEEE, 86(8): 1640-1659 (1998).

* cited by examiner

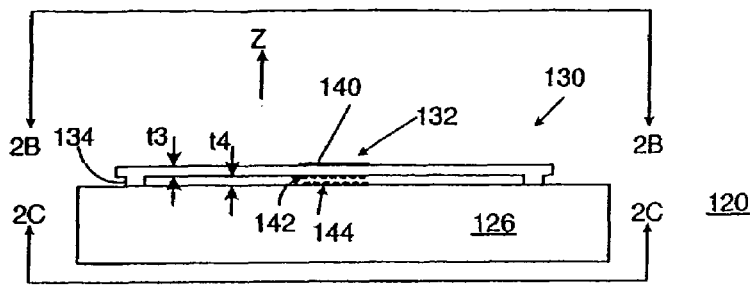
FIG. 2A
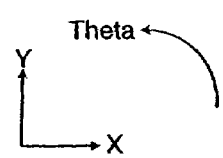
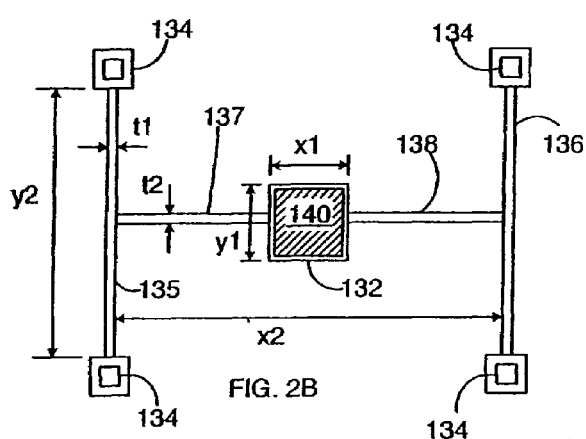
FIG. 2B
FIG. 2C
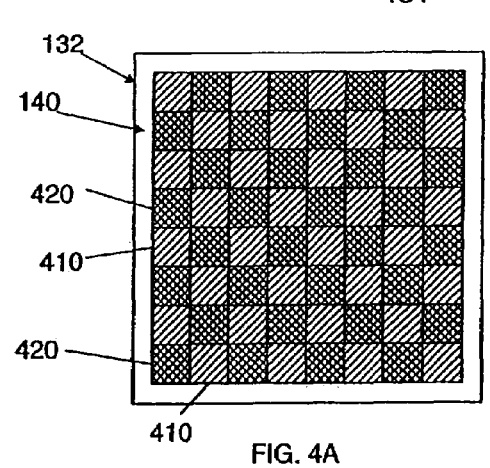
FIG. 4A
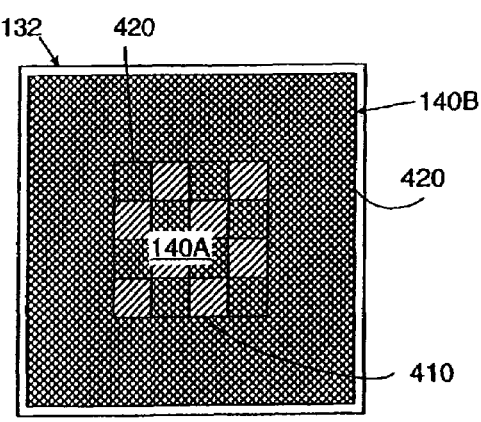
FIG. 4B
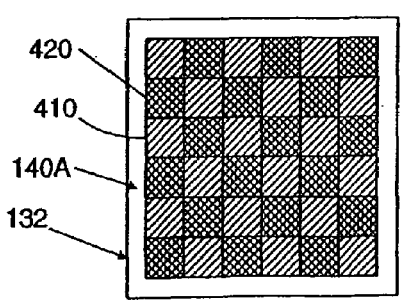
FIG. 4C
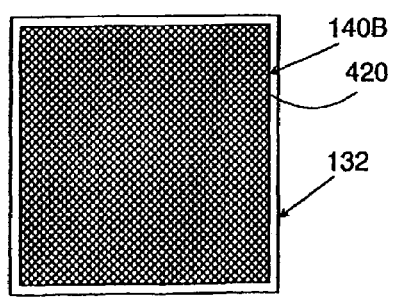
FIG. 4D

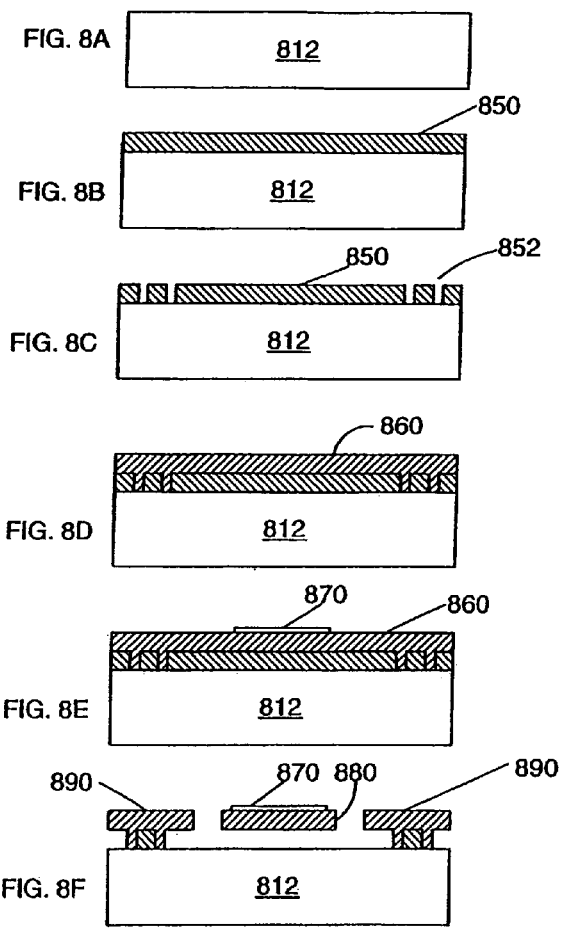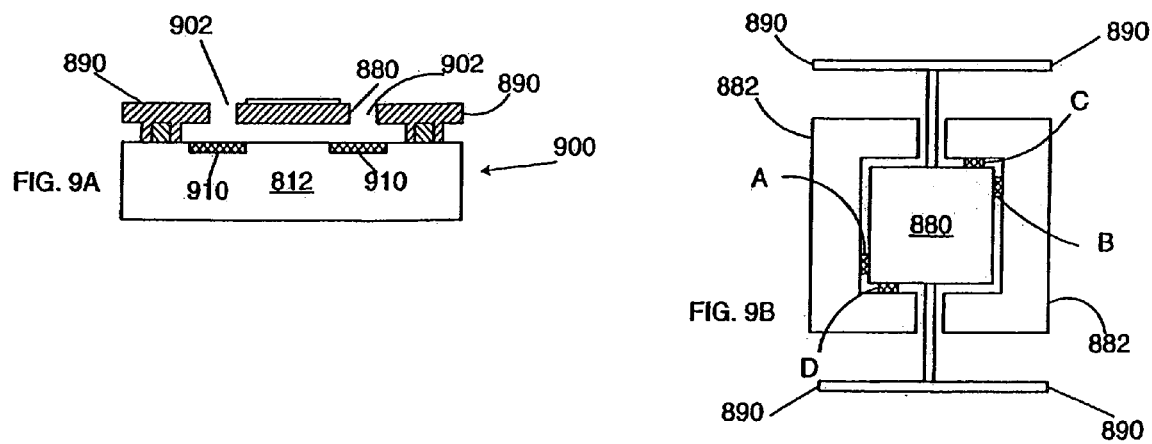

US 7,178,378 B2

RESONANT SENSOR AND SENSING SYSTEM

REFERENCE TO RELATED APPLICATIONS

This application is related to, and claims the priority of, U.S. Provisional Patent Application No. 60/406,808, which was filed on Aug. 29, 2002, and which is entitled DEVICE, APPARATUS, AND METHOD FOR SENSITIVE & ACCURATE DETECTION OF INTERACTING CHEMICAL AND BIOLOGICAL MATTER, and which is hereby incorporated by reference.

BACKGROUND OF THE INVENTION

The present invention relates to a sensing system. More specifically, the present invention relates to a MEMS (microelectromechanical system) based sensing system for measuring the properties of a sample, including detecting the presence of a measurand in a sample. As used herein, the term "measurand" means a particular kind of matter, organic or inorganic, such as a particular chemical, protein, virus, allergen, pathogen, molecule, analyte, etc., that is to be detected and/or measured.

Various types of sensing systems for measuring the properties of fluids (i.e., liquids and gases) are known in the art, such as, for example, systems for measuring the viscosity of oil. Additionally, various types of sensing systems for detecting the presence of a particular measurand are known in the art, such as, for example, systems for detecting the presence of protein molecules in a sample. MEMS based sensing systems have been developed. However, there remains a need for improved accurate, sensitive, reliable, inexpensive sensing systems.

SUMMARY OF THE INVENTION

These and other objects are provided by an improved MEMS based resonant sensor, which can exhibit two or more resonant modes. A plurality of such resonant sensors can be incorporated onto a single sensor chip. Activity of the resonant sensors can be sensed optically.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE FIGURES

For a fuller understanding of the nature and objects of the present invention, reference should be made to the following detailed description taken in connection with the accompanying drawings in which the same reference numerals are used to indicate the same or similar parts wherein:

FIG. 2A shows a side view of a sensor chip constructed according to the invention, which includes a single resonant sensor.

FIG. 2B shows a view of the resonant sensor taken along the line 2B—2B as shown in FIG. 2A.

FIG. 2C shows a view of the resonant sensor taken along the line 2C—2C as shown in FIG. 2A.

FIG. 4A shows the receptor area of a resonant sensor constructed according to the invention.

FIGS. 4B, 4C, and 4D show other embodiments of receptor areas constructed according to the invention.

FIGS. 8A–8F show products produced at various stages of yet another embodiment of a process for forming a sensor chip according to the invention.

FIGS. 9A and 9B show embodiments of a sensor chip constructed according to the invention that includes photodiodes in the substrate.

DETAILED DESCRIPTION OF THE INVENTION

Figure 1A:
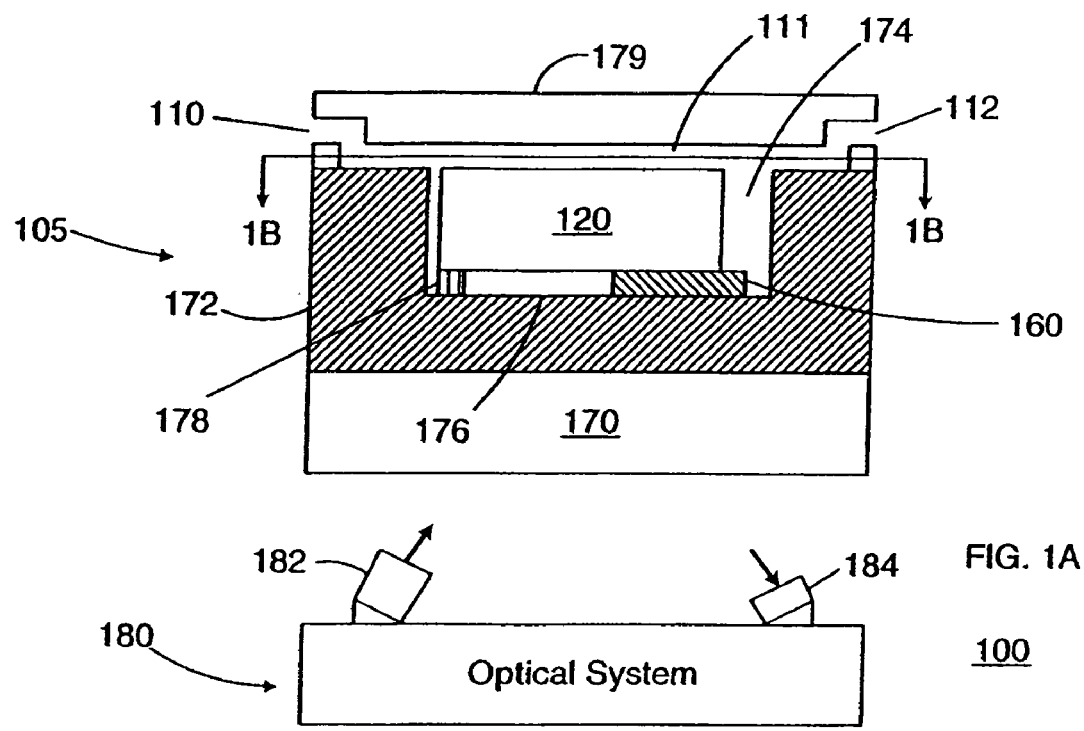
FIG. 1A shows a sectional side view of a sensing system constructed according to the invention.
Figure 1B:
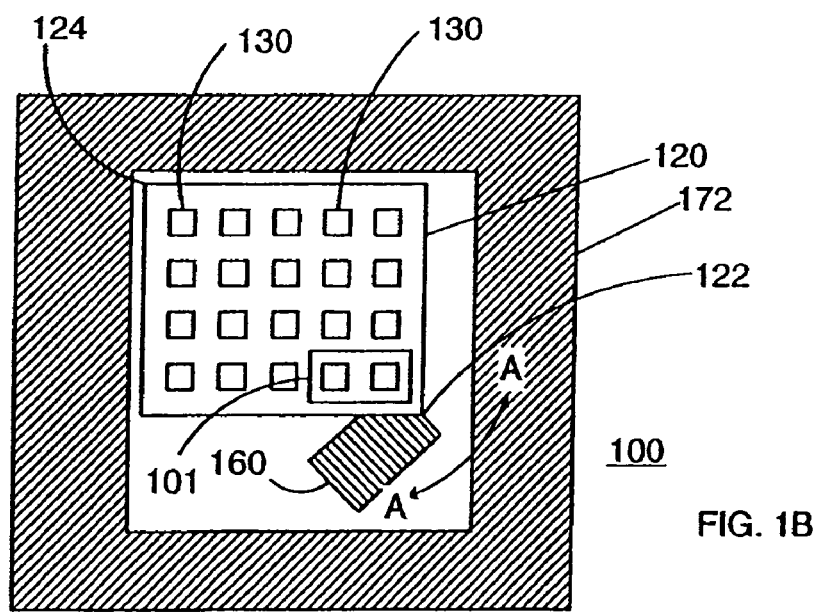
FIG. 1B shows a view of the sensing system taken along the line 1B—1B as shown in FIG. 1A.
Figure 3A:
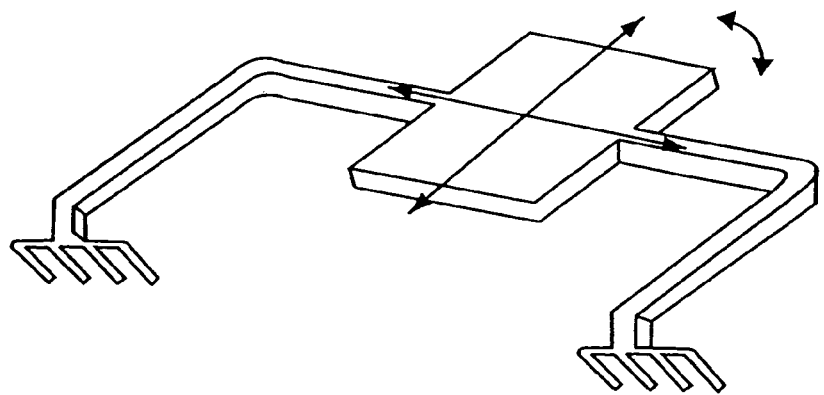
FIGS. 3A–3I each show another embodiment of a resonant sensor constructed according to the invention.
Figure 3B:
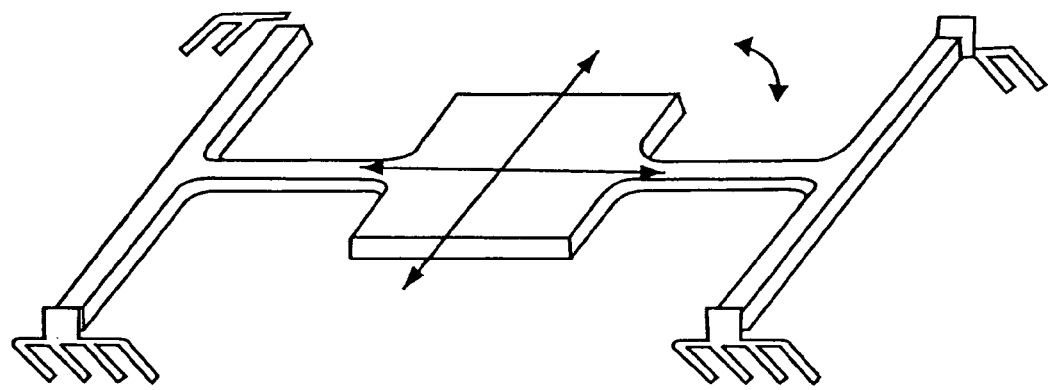
Figure 3C:
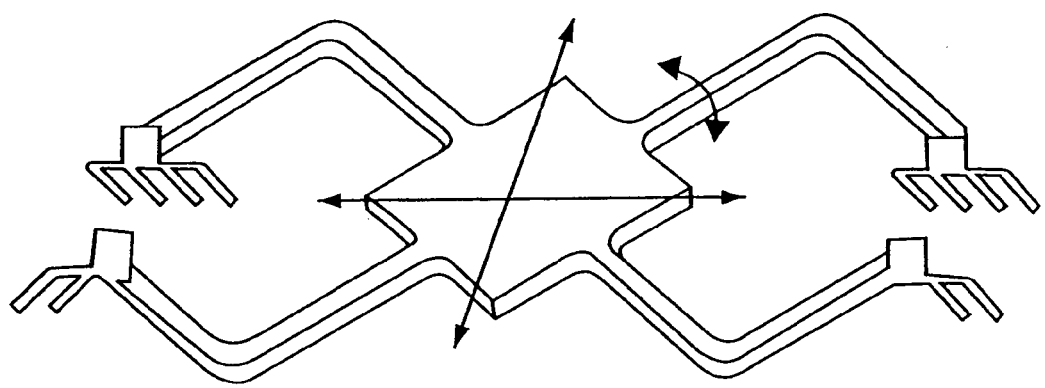
Figure 3D:
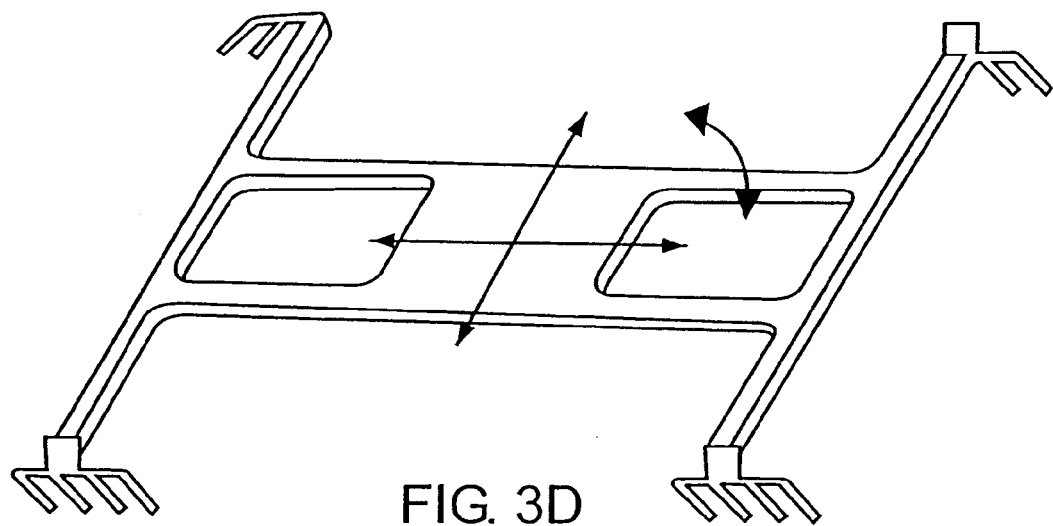
Figure 3E:
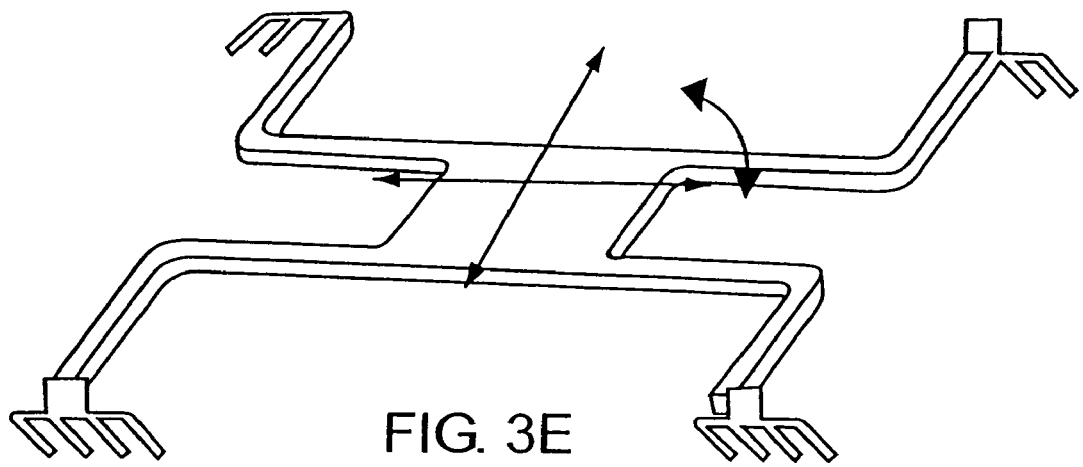
Figure 3F:
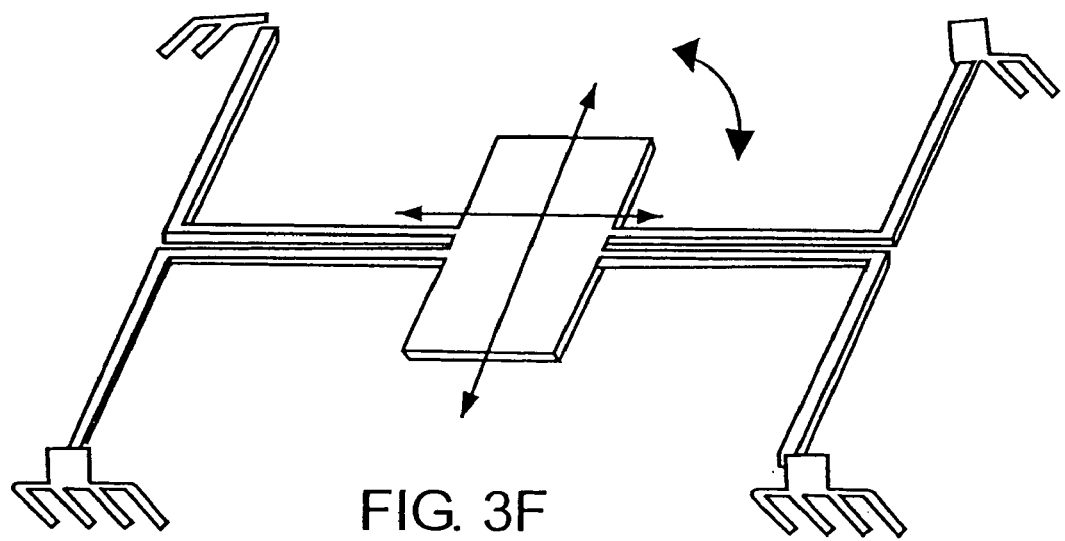
Figure 3G:
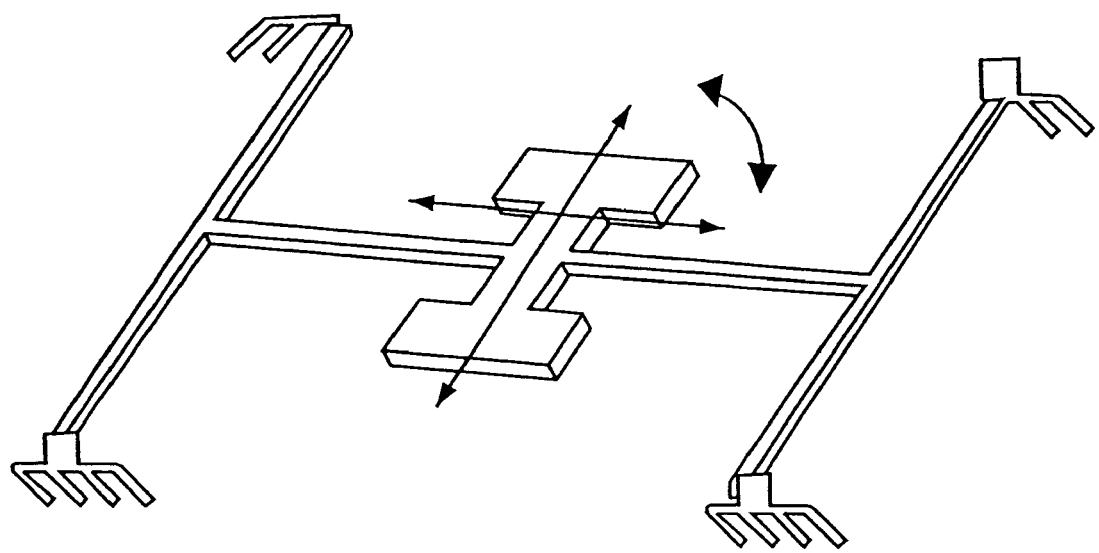
Figure 3H:
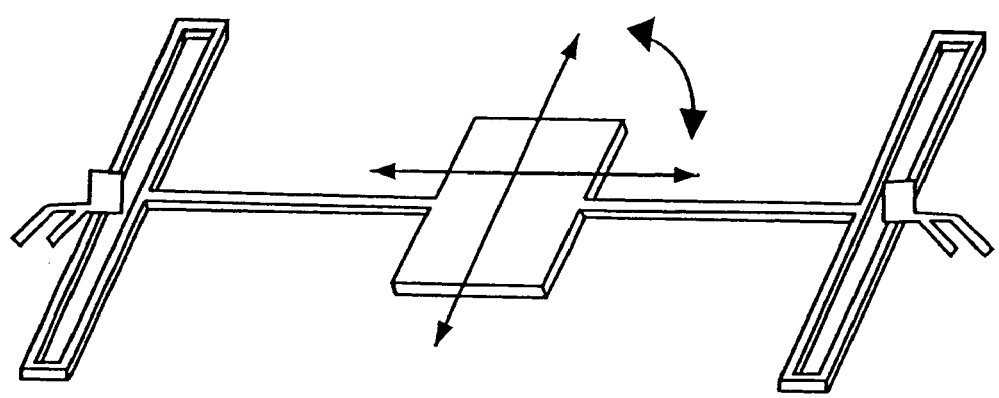
Figure 3I:
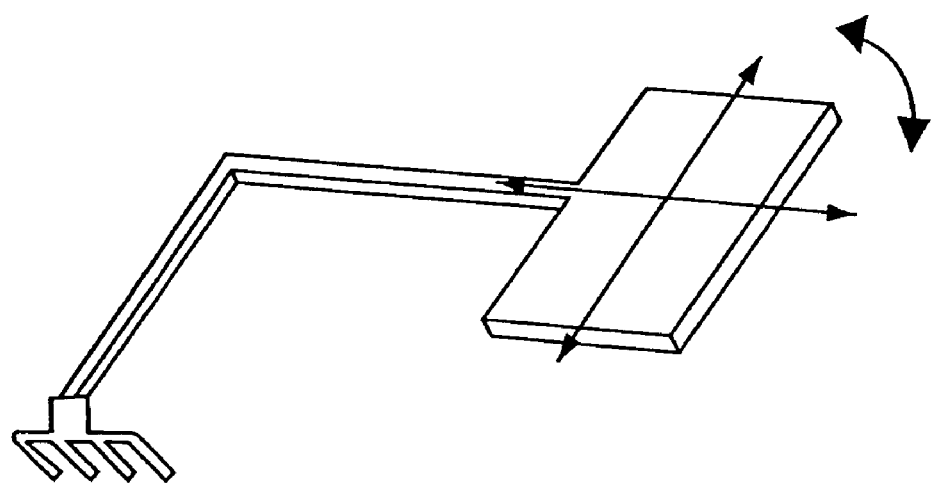

FIG. 1A shows a partially sectional side view of a sensing system 100 constructed according to the invention. FIG. 1B shows a view of sensing system 100 taken from the direction indicated by line 1B—1B as shown in FIG. 1A.

The operation and construction of sensing system 100 will be discussed in greater detail below. Briefly, sensing system 100 accurately detects the presence of a measurand in a sample. In operation, a liquid or gas sample flows through sensing system 100, entering system 100 at an inlet 110 and exiting system 100 at an outlet 112. Flowing the sample through system 100 exposes the sample to a sensor chip 120. As shown in FIG. 1B, sensor chip 120 includes a plurality of resonant sensors 130 (twenty such resonant sensors 130 being shown in FIG. 1B). Each of the resonant sensors 130 includes a moving member (or element) that can oscillate in one or more modes, or directions (e.g., x translation, y translation, and rotational movement in the theta direction). In one embodiment the resonant sensors 130 also include a receptor area on the moving member that selectively binds to a particular measurand. After sensor chip 120 has been exposed to the sample, an actuator 160 moves sensor chip 120 by a controlled minute amount thereby causing the moving members of the resonant sensors 130 to move in an oscillatory fashion. The motion of the moving members of the resonant sensors 130 is affected by the presence or absence of the measurand in the sample. That is, if the measurand was present in the sample, a tiny amount of the measurand will have bound to the receptor area of the resonant sensor, and the added mass of the bound measurand will affect the resonant frequency of the resonant sensor's moving member. An optical system 180 is used to measure the motion of the moving members of the resonant sensors 130. A data processor (not shown) analyzes signals provided by the optical system to determine the resonant frequencies of the moving members, and thereby determine whether the measurand is present in the sample. In addition, after the binding of one or more measurands in a sample to the receptor area and determining the resonant frequencies, the receptor area can be treated in a manner which causes one or more of the measurands to be released from the surface (e.g., an increase in temperature, or denaturant concentration). The resonant frequencies are then measured again to qualitatively or quantitatively analyze the release of the relevant measurands in response to the treatment.

By way of example, resonant sensors constructed according to the invention are capable of detecting a mass change of 0.05 pico grams (i.e., the system can detect the event of 0.05 pico grams of measurand binding to the receptor site of a resonant sensor). A single protein molecule is on the order of $3 \times 10^{-7}$ pico grams. Accordingly, measurement systems constructed according to the invention are capable of usefully detecting minute amounts of material (e.g., 150,000 protein molecules) in a sample.

As shown in FIG. 1A, sensing system 100 includes two main components: a mechanical system 105 and an optical system 180. Mechanical system 105 includes an optically transmissive (i.e., transparent at a particular wavelength or range of wavelengths of interest) substrate 170 and an optically transmissive mount 172, which is attached to the upper surface of substrate 170. Mount 172 defines a cavity, or well 174, which is bounded by a lower surface 176. Actuator 160 and an anchor 178 are attached to the lower surface 176 of mount 172. Sensor chip 120 is attached to actuator 160 and anchor 178 and is disposed generally within the well 174. A cover 179 is attached to the top of mount 172 so as to define the sample inlet 110, the sample outlet 112, and a channel 111 through which the sample may flow from the inlet to the outlet (or, since direction of flow does not affect operation of the sensing system, from the outlet to the inlet). When the sample flows through channel 111, the sample is exposed to the resonant sensors 130, which are disposed near the top of sensor chip 120.

In operation, when actuator 160 is activated, the actuator 160 moves one corner 122 of sensor chip 120 by a controlled minute amount in a direction suggested by the arrow A—A shown in FIG. 1B. Anchor 178 supports the opposite corner 124 of sensor chip 120 such that chip 120 pivots about anchor 178.

The optical system 180 includes a light generator (e.g., a laser) 182 and a light detector (e.g., a photodiode) 184. The optical system 180 may be moved so as to address the plurality of resonant sensors 130 one at a time. When one of the resonant sensors 130 has been so addressed, light emitted by light generator 182 is incident on the resonant sensor and light reflected by the resonant sensor is received by light detector 184. The light detector 184 generates an output signal representative of the light received by the detector. Sensing system 100 measures the motion of the moving element of the resonant sensor by monitoring the output signal generated by light detector 184.

FIG. 2A shows a side view of a sensor chip 120 constructed according to the invention. The sensor chip 120 shown in FIG. 2A includes only one resonant sensor 130. However, as discussed above (and as indicated generally in FIG. 1B), sensor chips 120 constructed according to the invention can include a plurality of resonant sensors 130. For convenience of illustration and discussion, sensor chips containing a single sensor 130 will be discussed primarily herein. However, it will be appreciated that the discussions of construction and operation of single resonant sensor chips are generally applicable to multi resonant sensor chips as well. It will further be appreciated that sensor chip 120 is constructed using micromachining processes typically found in the production of a MEMS (microelectromechanical systems) device. As a MEMS device, sensor chip 120 may, but need not, include any electrical devices (e.g., transistors, photodiodes). Rather, sensor chip 120 includes miniaturized mechanical devices that are formed using the techniques normally used to form electronic integrated circuits (e.g., photolithography).

As shown in FIG. 2A, sensor chip 120 includes an optically transmissive substrate 126. Resonant sensor 130 is mounted to the upper surface of substrate 126. FIG. 2B shows a view of resonant sensor 130 taken in the direction of arrow 2B—2B as shown in FIG. 2A. FIG. 2C shows a view of resonant sensor 130 taken in the direction of arrow 2C—2C as shown in FIG. 2A. For convenience of illustration, the substrate 126 is not shown in FIGS. 2B and 2C.

Resonant sensor 130 includes a central moving member 132 and four anchors 134. The left pair of anchors 134 are connected by a tether 135 that extends in a Y direction (the Y direction being indicated in FIG. 2C). The right pair of anchors 134 are connected by another tether 136 that also extends in the Y direction. A tether 137, which extends in the X direction (the X direction being substantially perpendicular to the Y direction and being indicated in FIG. 2C), extends from tether 135 to the left side of central moving member 132. A tether 138, which also extends in the X direction, extends from tether 136 to the right side of central moving member 132.

As shown in FIG. 2A, the four anchors 134 are fixed to the upper surface of substrate 126. However, the tethers 135, 136, 137, 138, and the central moving member 132 are spaced apart from the substrate 126 in the Z direction (the Z direction being substantially perpendicular to the X and Y directions, and being illustrated in FIG. 2A). The tethers are also somewhat elastic. This construction allows the central moving member 132 to move, and in particular to oscillate, with respect to substrate 126.

The upper surface of central moving member 132 defines a receptor area 140. The construction and operation of receptor area 140 will be discussed further below. Briefly, receptor area 140 is configured to provide binding, or receptor, sites for a particular measurand.

As shown in FIGS. 2A and 2C, the bottom surface of the central moving member 132 defines an optical grating 142 (formed by a plurality of reflective stripes). Also, the upper surface of substrate 126 defines an optical grating 144. As will be discussed further below, gratings 142 and 144, which may be made from stripes of a reflective metal such as aluminum, allow optical measurement of the position of the central moving member 132 (e.g., as discussed Yaralioglu, G. G., Atalar, A., Manalis, S. R., and Quate, C. F., "Analysis and design of an interdigital cantilever as a displacement sensor," J. Applied Physics, Vol. 83, No. 12, 1998.). Other grating types can be used, such as, for example, phase gratings.

Referring to FIGS. 2A and 2B, the height of the central member 132 as measured in the Y direction is designated y1, the width of the central member 132 as measured in the X direction is designated x1, the height of the tethers 135, 136 as measured in the Y direction is designated y2, and the distance between the tethers 135 and 136 as measured in the X direction is designated x2. Also, the thickness of the tethers 135, 136 as measured in the X direction is designated t1, the thickness of the tethers 137, 138 as measured in the Y direction is designated t2, the thickness of the tethers as measured in the Z direction is designated t3, and the spacing between the tethers and the substrate 126 as measured in the Z direction is designated t4. In one embodiment, the resonant sensor is made primarily from silicon and x1 is substantially equal to thirty microns (i.e., 30×10 to the minus sixth power meters), y1 is substantially equal to sixty microns, y2 is substantially equal to one hundred microns, and x2 is substantially equal to 150 microns. In that embodiment, t1, t2, t3, and t4 are substantially equal to two microns. This configuration results in primary, in-plane, resonances (i.e., resonances measured in the X, Y, and theta directions) spanning 0.1 to 10 MHz (Mega Hertz). This maximizes signal to noise and allows for adequate frequency determination resolution within integration periods on the order of one second. These resonant modes respond with oscillatory motions on the order of 100 nm (nanometers) to one mm (millimeter) when excited by motions of the substrate 126 on the order of one nm in amplitude. In the configuration shown, out of plane modes (e.g., oscillation in the Z direction) are damped due to the close proximity of the moving element 132 and the substrate 126. In this embodiment, the optical grating 142 may be made by ten stripes of aluminum, each stripe being about two microns wide, and each pair of adjacent stripes being separated by about two microns. Optical grating 144 may be similarly configured although it may be advantageous for grating 144 to extend over a larger range than grating 142 so that all of grating 142 is always disposed opposite some portion of grating 144 even when moving member 132 has moved to the extreme ends of its range of motion.

It will be appreciated that the dimensions and measurements discussed above merely provide an example embodiment and that considerable variation is possible. FIGS. 3A–3I illustrate alternative useful geometric configurations for resonant sensor 130. In a sensor chip 120 made according to the invention, all the resonant sensors may be made using the same geometric configuration (e.g., all may be configured as shown in FIGS. 2A–2C), or alternatively, different resonant sensors on the same chip may be constructed using different geometric configurations (e.g., half the resonant sensors may be configured as shown in FIGS. 2A–2C and the remaining half of the resonant sensors may be configured using one or more of the configurations shown in FIGS. 3A–3I).

In operation, the substrate may be moved in an oscillatory fashion at a low frequency, such as between 0.1 and 10 MHz, by controlled minute amounts (e.g., by the actuator 160 shown in FIGS. 1A and 1B). This motion of the substrate excites motion of the moving members of the resonant sensors. The resonant frequency of the moving member 132 is a function of the mass of the central member 132. If a measurand binds to the receptor area 140 of the central member, the added mass of the measurand changes the frequency at which the moving member exhibits resonance. Similarly, if a measurand is released from the receptor area 140 of the central member, the subtracted mass of the measurand changes the frequency at which the moving member exhibits resonance. Accordingly, the presence or absence of a measurand in a sample may be detected by monitoring the resonant frequency of the central member after the sensor has been exposed to the sample. For example, the presence of the measurand may be detected generally according to the following Equation (1)

$$\frac{\Delta M}{M} \propto \frac{\Delta f_{resonance}}{f_{resonance}} \quad (1)$$

in which M is the mass of central member 132, $\Delta M$ is the change in mass when the measurand binds to the central member 132, $f_{resonance}$ is the frequency at which the central member 132 exhibits resonance when no measurand is bound to the receptor area 140, and $\Delta f_{resonance}$ is the change in resonance frequency caused by having a measurand (of mass $\Delta M$) bound to the receptor area 140. Equation (1) provides an idealized expression relating mass change to frequency change, and such an idealized viewpoint further includes a similar expression for each mode of the resonator.

The moving member 132 of the sensor 130 shown in FIGS. 2A–2C exhibits multi modal resonance. That is, the motion of central moving member 132 may be resolved into three distinct oscillating movements: e.g. substantial oscillation in the X direction, substantial oscillation in the Y direction, and substantial oscillation in the theta direction (i.e., rotational oscillation). Modes consisting of independent combinations of directions are also possible by design. Since the central moving member is disposed close to the substrate, out of plane resonant modes (e.g., resonant motion in the Z direction) are limited by the dissipation provided by the fluid in this gap. Allowing the central moving member to oscillate in more than a single mode advantageously improves the noise immunity of system 100. Ideally, presence or absence of a measurand bound to the receptor area is the only factor that affects the resonant frequency of the central moving member. However, environmental factors (e.g., temperature) also affect the resonant frequency of the central moving member. Providing multi modal resonance improves noise immunity since oscillation in some directions may be more affected by environmental factors than oscillation in other directions and the environment influences can be resolved independent of measurand influences.

By way of example, tethers that extend in the Y direction (135, 136) exhibit distinct changes in structural response due to thermal influences as compared with the tethers that extend in the X direction (137, 138). Both reflect the same changes in stiffness due to modulus changes induced by temperature change. However, tethers 135, 136 are effectively clamped to the substrate at either end, and are subject to changing tension (or compression) that results from differential expansion between the substrate and the tether material. This stress is relieved in tethers 137, 138 by the bending of tethers 135, 136. Thus the Y translation mode of the moving member 132 will have larger relative shift in resonance frequency due to temperature change than X translation mode. Both will yield the same relative shift due to measurand mass loading. So, by measuring both resonant frequency changes (i.e., changes in resonant frequency of the moving member 132 in both the X and Y directions) the influence of the measurand can be distinguished from temperature induced effects.

For convenience of illustration, FIGS. 2A and 2B show the central moving member 132 defining a receptor area 140 that is uniformly distributed over the member 132. However, the receptor area 140 normally has a more complex construction. FIG. 4A shows a conceptualized view of a receptor area 140 distributed over a single central moving member 132. As indicated, receptor area 140 includes an array of binding sites 410 interspersed with an array of a blocking site 420. The detailed construction of binding sites 410, blocking sites 420, and the rational for including blocking sites 420 will be discussed below. It should be appreciated that scale of the individual receptor and blocking sites is far smaller than illustrated in FIG. 4A. Each receptor site 410 is normally of a size similar to a single molecule of the measurand, and each blocking site 420 is similarly sized. It should also be appreciated that some embodiments may include binding and/or blocking material coatings on at least portions of sensor components other than the central moving member 132. One exemplary embodiment includes tethers coated with a blocking material to prevent an undesired accumulation of material on those tethers. In general, the blocking materials and the binding materials are not necessarily limited to the central moving member of the sensor.

Ideally, only a preselected measurand will bind to the binding sites 410 and nothing in the sample will bind to areas of the moving member 132 other than the binding sites 410. However, unwanted material from the sample (e.g., protein) typically will bond to the moving member 132 at sites other than the binding sites 410. Blocking sites 420 are included to reduce the amount of material from the sample that binds to the moving member 132 at sites other than the receptor sites 410. Again, ideally, nothing will bind to the blocking sites 420. However, although the blocking sites 420 reduce the amount of material that binds to areas of the moving member 132 other than the receptor sites 410, some material from the sample still generally binds to the blocking sites 420. FIG. 4B shows one strategy for constructing the receptor area 140 such that it allows discrimination between the effect of the measurand and unwanted material that binds to the blocking sites. As shown in FIG. 4B, two separate receptor areas are provided on the moving member 132: a first receptor area 140A and a second receptor area 140B. The first receptor area 140A is centered on the moving member 132. Like the receptor area 140 shown in FIG. 4A, the first receptor area 140A includes an array of binding sites 410 interspersed with an array of blocking sites 420. However, the first receptor area 140A does not extend to the outer periphery of the moving member 132 and is instead disposed proximal to the center of the member 132. The second receptor area 140B includes only a blocking site 420 and is disposed around the periphery of the first receptor area 140A.

In operation, if unwanted material binds to the blocking sites 420 in the first receptor area 140A, the same type of unwanted material will also likely bind to the second receptor area 140B. Due to its distance from the center of the moving member 132, the mass of material binding to the second receptor area 140B will have a pronounced effect on the rotational resonant mode of the sensor 130 (i.e., oscillation of the central moving member in the theta direction). This allows the measurement system to distinguish between the measurand binding to the binding sites 410 and unwanted material binding to the blocking sites 420.

A brief discussion of four possible cases illustrates generally how the receptor area configuration shown in FIG. 4B can be used to provide useful discrimination. In the first case, there is substantially no measurand in the sample and nothing from the sample binds to the blocking sites 420. In this case, the resonant frequency of the moving member is substantially unchanged by exposure to the sample. In the second case, measurand is present in the sample and substantially nothing in the sample binds to the blocking sites 420. In this case, the measurand will bind to the receptor sites 410 thereby changing the resonant frequency of the moving member in the X and Y directions. Since exposure to the sample does not result in adding mass to blocking sites 420, the rotational oscillation frequency experiences only a relatively small change by exposure to the sample. In the third case, there is substantially no measurand in the sample but material from the sample does bind to the blocking sites 420. In this case, the mass of the material that binds to the blocking sites 420 affects the resonant frequency of the moving member in the X, Y, and theta directions. In the fourth case, there is measurand in the sample and material from the sample also binds to the blocking sites 420. In this case, the mass of material binding to the receptor and blocking sites 410, 420 affects the resonant frequency of the moving member in the X, Y, and theta directions. The results of the third and fourth cases are similar, however the change in resonant frequency in the X and Y directions will be greater in the fourth case than in the third (i.e., because of the added mass of the measurand bound to the receptor sites 410). It will be appreciated that while considerable variation is possible, these four cases set forth a basic strategy for discriminating between measurand binding to the receptor sites 410 and unwanted material binding to the blocking sites 420. The table below summarizes these cases.

| | Resonant frequency measured in a particular direction | | |
|---|---|---|---|
| | X | Y | Theta |
| Case 1: No Measurand in sample, and no material from sample binds to blocking sites | Unchanged by exposure to sample | Unchanged by exposure to sample | Unchanged by exposure to sample |
| Case 2: Measurand present in the sample (and binds to receptor sites 410) and no material from sample binds to blocking sites | Changed by exposure to sample | Changed by exposure to sample | Changed by small amount due to exposure to sample |
| Case 3: Measurand not present in the sample but material from sample binds to blocking sites | Changed by exposure to sample | Changed by exposure to sample | Changed by large amount due to exposure to sample |
| Case 4: Measurand present in the sample and material from sample | Changed by large amount | Changed by large amount due | Changed by large amount due |

-continued

| | Resonant frequency measured in a particular direction | | |
|---|---|---|---|
| | X | Y | Theta |
| binds to blocking sites | due to exposure to sample | to exposure to sample | to exposure to sample |

FIGS. 4C and 4D show an alternate strategy for discriminating between measurand binding to the binding sites 410 and unwanted material in the sample binding to the blocking sites 420. FIG. 4C shows the central moving member 132 of one resonant sensor 130 and FIG. 4D shows the central moving member 132 of another resonant sensor 130. The two resonant sensors 130 shown in FIGS. 4C and 4D may be formed on the same sensor chip 120. The moving member 132 shown in FIG. 4C has a receptor area 140A, and the moving member 132 shown in FIG. 4D has a different receptor area 140B. Receptor area 140A includes arrays of binding sites 410 and blocking sites 420 that are centrally disposed on the moving member. Receptor area 140B includes only a blocking site 420 disposed over substantially the entire moving member 132. Comparing the response of the two sensors 130 (i.e., the sensors shown in FIGS. 4C and 4D) allows the sensing system to distinguish the effect of measurand binding to binding sites 410 from the effect of unwanted material binding to the blocking sites 420. This may be done using a similar strategy to the one discussed above in connection with FIG. 4B. It will be appreciated that numerous other configurations may also be used to facilitate discriminating between the effect of measurand binding to the binding sites 410 and the effect of unwanted material binding to the blocking sites 420. Similar strategies may also be used to discriminate between the effect of measurand binding to the binding sites and other environmental factors or noise (e.g., temperature changes in the ambient environment).

Figure 12A:
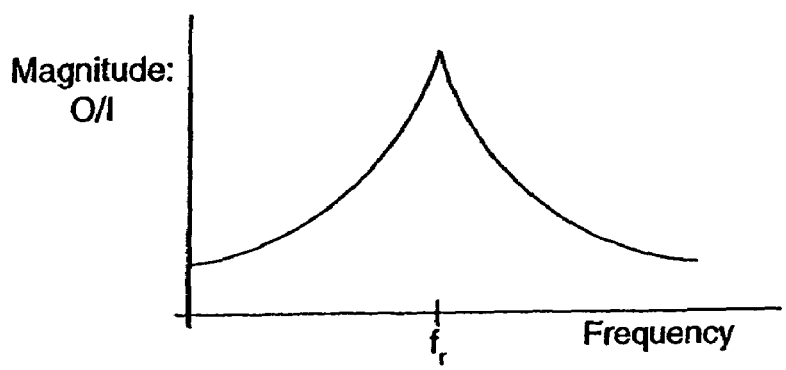
FIG. 12A shows the amplitude of the frequency response of a single resonant sensor.
Figure 12B:
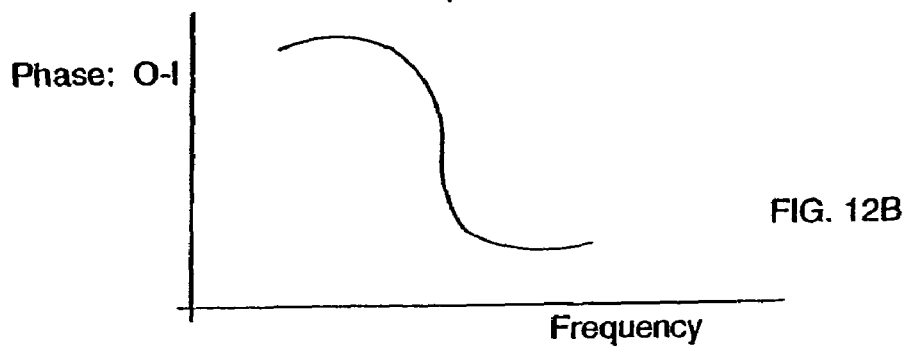
FIG. 12B shows the phase of the frequency response of a single resonant sensor.

As has been discussed above, sensing system 100 can detect the presence of a particular measurand in a sample by monitoring the resonant frequencies of the resonant sensors 130 after the system has been exposed to the sample. The simple method of monitoring only the resonant frequency of the resonant sensors is an effective way to use sensing system 100. However, it also represents a simple, degenerate, case of the information that may be obtained from sensing system 100. A more complete representation of this information is shown in FIGS. 12A and 12B, which are graphs showing the magnitude and phase of the frequency response of a single resonant sensor 130, as measured in a particular direction (e.g., the X direction). Before discussing how the information presented in FIGS. 12A and 12B may be used, the manner in which the graphs are generated will be explained.

Referring back to FIGS. 2A–2C, if the substrate 126 is moved in an oscillatory fashion at a particular frequency, the moving member 132 of the resonant sensor 130 will also begin to move in an oscillatory fashion at substantially the same frequency. However, two significant parameters of the resonant sensor 130 will vary depending on the oscillation frequency of the substrate 126: (1) the ratio of the amplitudes of the oscillation of the moving member 132 and the oscillation of the substrate 126, or the "magnitude" of the frequency response and (2) the phase difference between the oscillation of the moving member 132 and the oscillation of the substrate 126, or the "phase" of the frequency response.

FIG. 12A shows the magnitude of the frequency response (i.e., for a range of oscillation frequencies of the substrate 126, it shows the amplitude of the oscillation of the moving member 132 divided by the amplitude of the oscillation of the substrate 126). FIG. 12B shows the phase of the frequency response (i.e., for a range of oscillation frequencies of the substrate 126, it shows the difference in phase between the oscillation of the moving member 132 and the oscillation of the substrate 126). Also, as noted above, the frequency response illustrated in FIGS. 12A and 12B represent the response as measured in a particular direction, such as the X direction. For a resonant sensor 130 that exhibits three principle resonant modes (e.g., oscillation in substantially the X, Y, and theta directions), three sets of graphs, of the form of the graphs shown in FIGS. 12A and 12B, can be generated to fully characterize the frequency response of the resonant sensor 130 (i.e., one set showing the amplitude and phase responses in each of the X, Y, and theta directions).

As shown in FIG. 12A, the magnitude of the frequency response (at least as measured in a single direction) exhibits a peak at the resonant frequency $f_r$. Also, as shown in FIG. 12B, the phase of the frequency response exhibits a rapid change near the resonant frequency $f_r$. If FIGS. 12A and 12B represent the amplitude and phase of the frequency response for oscillation of the moving member 132 in the X direction, graphs illustrating the response of the moving member in the Y and theta directions would generally look similar in character to FIGS. 12A and 12B, but would typically exhibit a peak at a different resonant frequency (i.e., different than $f_r$).

FIGS. 12A and 12B represent the frequency response of a resonant sensor 130 under a particular condition. For example, FIGS. 12A and 12B may show the frequency response of a resonant sensor 130 before the sensing system 100 has been exposed to a sample containing the measurand. Exposing the sensing system 100 to a sample containing the measurand will change the frequency response of the sensor 130 (i.e., the frequency response will change in response to having some of the measurand bind to the receptor area of the moving member 132). For example, after exposure to a measurand containing sample, the frequency response of the sensor will normally be similar to the pre-exposure response, but the frequencies at which resonance occurs will be changed (i.e., resonant peak will be at $f_r$+delta).

As noted above, presence of the measurand in the sample can be detected simply by monitoring the resonant frequencies of the moving member 132 of the resonant sensor 130. Similarly, presence of the measurand in the sample can be detected simply by monitoring the frequency response of the resonant sensor 130 at a particular oscillation frequency (e.g., by oscillating the sensor chip at a particular, constant, frequency, and by monitoring the frequency response of the resonant sensors at that frequency).

However, instead of monitoring the frequency response at a particular, constant, frequency, it may be advantageous to monitor the frequency response of the resonant sensors over a range of frequencies. This advantageously allows a decision as to whether the measurand is present in the sample to be based on a collection of data points rather than a single, or a small number of, data points. Or in other words, instead of examining isolated data points, this technique allows examination of functions over a range. For example, the amplitude and phase of the frequency response of a resonant sensor can be measured over a range of frequencies and that measured response can be compared with one or more sets of previously determined frequency responses, or curve fit functions thereof. Each of the frequency responses is a function of the oscillation frequency of the substrate and other variables. The previously determined frequency responses can represent a variety of cases, such as the case in which (1) the sensing system has not been exposed to any sample and is in a "just manufactured" state; (2) the sensing system has been exposed to a sample containing the measurand, and in which the sample is of the type that does not cause binding to the blocking sites of the receptor area; and (3) the sensing system has been exposed to the sample containing the measurand, and in which the sample is of the type that does cause binding to the blocking sites of the receptor area. It will be appreciated that frequency responses, or curve fit functions thereof, for many other cases may be prepared in advance and that in operation the measured frequency response can be compared against these responses and functions. The decision about which case actually represents the conditions experienced by the sensing system may be made by comparing the measured frequency response with that of the previously determined cases and selecting the best match.

It will also be appreciated that the previously determined frequency responses can be prepared using one or more control resonant sensors. The control resonant sensors may be manufactured by the same process used to produce resonant sensors that are later used to test for the presence of a particular measurand such that they exhibit substantially similar frequency responses. Alternatively, such control resonant sensors need not be used and the previously determined responses can be measured using the same sensors that are later used to detect the presence or absence of a measurand in a sample.

It will also be appreciated that multiple sensors can be configured with different receptor molecules for the same measurand. For example, different antibodies specific for different epitopes of a single measurand can be employed. This is useful for increasing the confidence in the detection of the measurand.

Numerous methods for using sensing system 100 to detect the presence of a measurand in a sample have been discussed above. In addition to detecting the presence of a measurand, sensing system 100 may be used more generally to measure properties of a sample. For example, if sensing system 100 is submerged in an oil, sensing system 100 may be used to determine the oil's viscosity. Whereas measurand binding to the receptor area adds mass to a moving member 132 of a resonant sensor 130, oil surrounding a resonant sensor 130 provides resistance to the motion of the central moving member 132 (even if none of the oil binds to the sensor, and even if the sensor does not include a receptor area for selective binding). The amount of resistance added by the oil is a function of the oil's viscosity. So, the oil's viscosity can be measured by monitoring the manner in which motion of the moving member is affected by presence of the oil. In general, sensing system 100 may be used to measure interaction between a sample (e.g., oil, a gas that may contain a particular measurand, etc.) and one or more resonant sensors 130.

Figure 5:
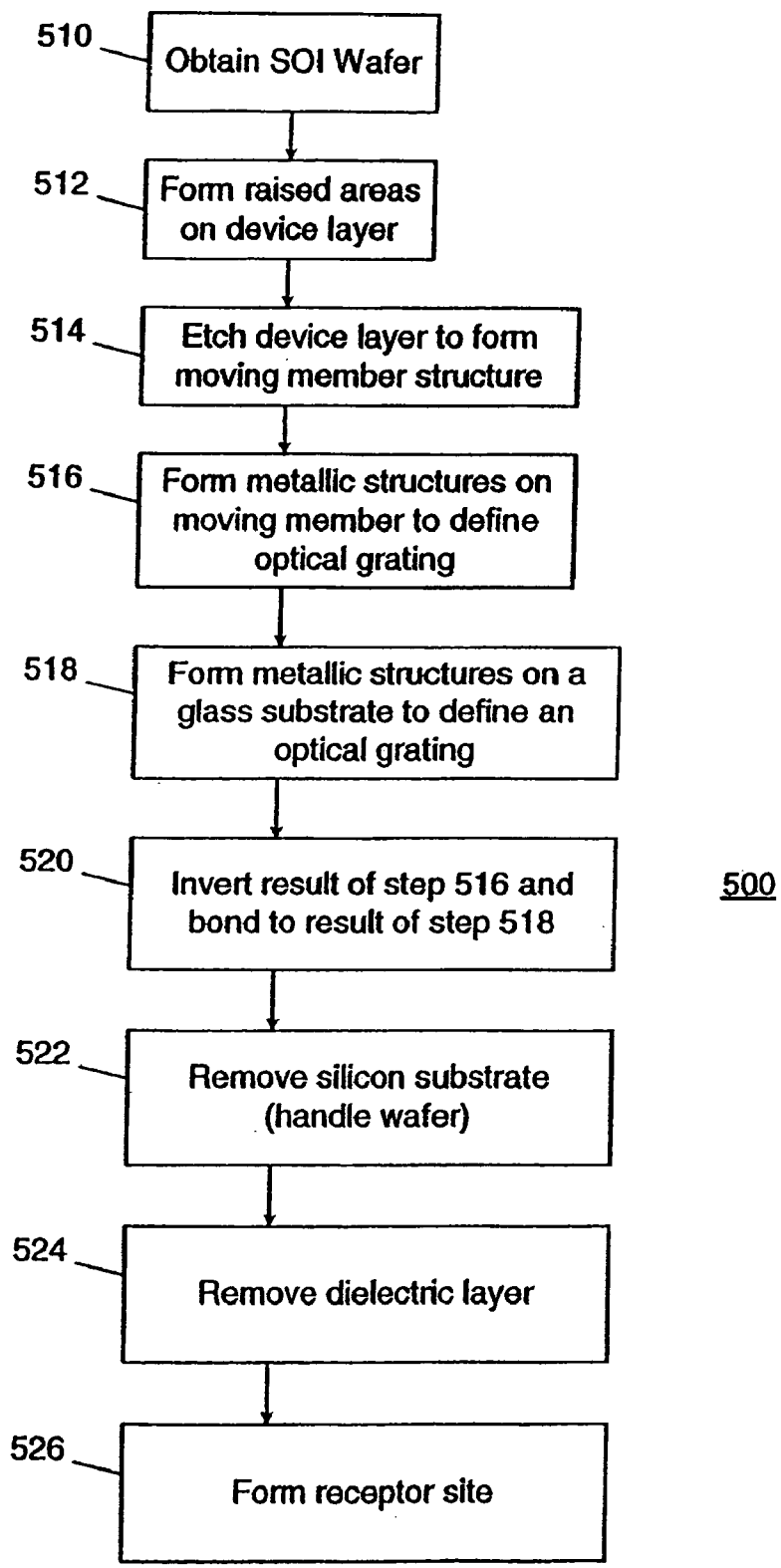
FIG. 5 shows a flow chart of a process for forming a sensor chip according to the invention.

FIG. 5 shows a flow chart describing a process 500 for manufacturing sensing chip 120. FIGS. 6A–6I show intermediate products produced at various stages of process 500.

Figure 6A:
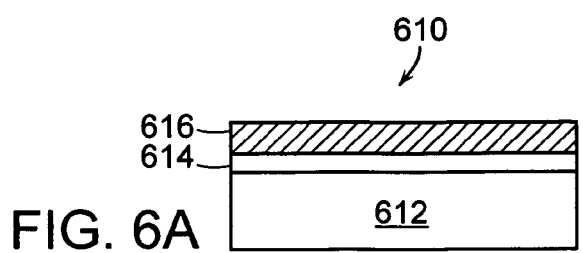
FIGS. 6A–6J show products produced at various stages of the process illustrated in FIG. 5.

The first step 510 in process 500 is to provide a silicon-on-insulator (SOI) wafer. Such a SOI wafer 610 is shown in FIG. 6A. As shown, wafer 610 includes a silicon substrate 612, a dielectric layer 614 such as silicon dioxide overlying the substrate 612, and a silicon device layer 616 (e.g., single crystal silicon) overlying the dielectric layer 614. In one embodiment, the device layer 616 may be four microns thick, the dielectric layer 614 may be three microns thick, and the substrate 612 may be about five hundred microns thick.

Figure 6H:
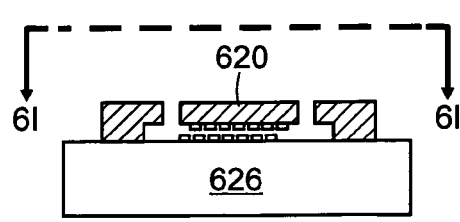
Figure 6B:
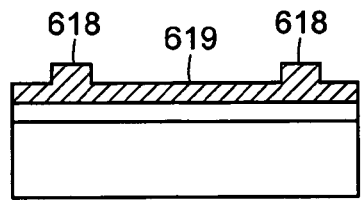
Figure 6C:
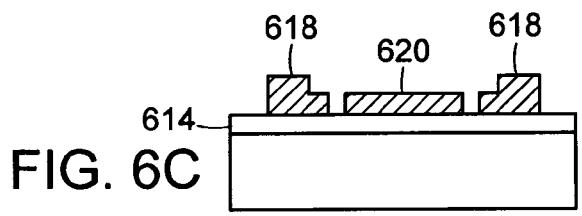

The second step 512 in process 500 is to form raised areas in the device layer. FIG. 6B shows the result of this step. As shown, device layer 616 now defines raised areas 618. The raised areas 618 may stand about two microns above a lower surface 619 of device layer 616. At a later stage of processing, the raised areas 618 will be used to form the anchors 134 shown in FIGS. 2A–2C. The raised areas 618 may be formed using conventional photolithographic processing. For example, a timed etch may be used to etch to a depth of two microns portions of the device layer that have not been covered with photoresist. A reactive ion etcher (RIE) and a photoresist mask is suitable for this step. Alternatively, a crystallographic silicon etch can also be used. Another etch step can be inserted at this point to provide features on the surface 619, which after more processing will become the bottom of the moving member, to prevent stiction after fabrication is complete. These features would be small protrusions to limit the contact area should the moving member touch the substrate, limiting the bonding force such that it is less than the restoring force of the tethers. This step would use the same photoresist masking and RIE steps as previously described. The next step 514 in process 500 is to define the silicon structure that will later form the moving member by etching through the device layer 616 down to the dielectric layer 614. The result of this step is shown in FIG. 6C. As shown, after this step the raised areas 618 remain but portions of the device layer have been removed to define the structure 620. Although structure 620 is presently fixed to dielectric layer 614, at later steps in process 500, structure 620 will become the central moving member (e.g., as shown at 132 in FIG. 2B). This processing step 514 uses photoresist to protect from the etch the following structures: raised areas 618, which will become the anchors; structure 620, which will become the moving member; and the tethers (not shown in FIG. 6C, but shown in FIG. 6I) that connect structure 620 to the anchors. A reactive ion etch is suitable for performing the etch of this step 514, and the dielectric layer 614 may act as an etch stop.

Figure 6I:
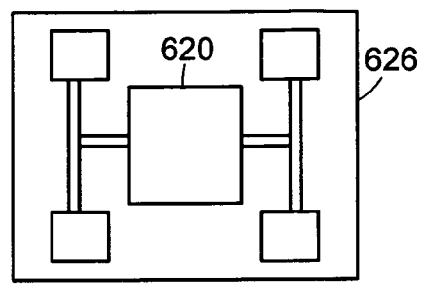
Figure 6D:
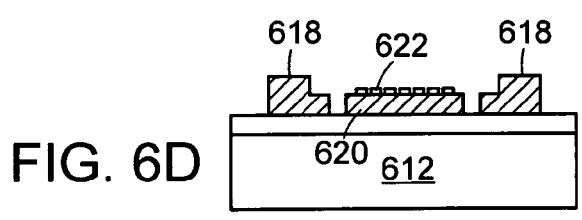

The next step 516 in process 500 is to form metallic structures on structure 620. The result of this step is shown in FIG. 6D. As shown in FIG. 6D, metallic stripes 622 have been formed on structure 620. Metallic stripes 622 form an optical grating used for sensing the position of the moving member. The stripes 622 may be formed from a reflective metal such as aluminum. One method of forming the stripes 622 is to (a) deposit photoresist on structure 620 in areas where it is not desired to form stripes 622; (b) deposit a thin layer of aluminum using an electron beam evaporator or similar system onto the structure 620 and the overlying photoresist; a thickness of 0.1 microns for the aluminum layer being adequate and then (c) soaking the wafer in solvent to remove the photoresist and metal that overlies the photoresist, thereby leaving the desired stripes 622. This method of forming the stripes 622 may be called a "lift off" method since unwanted portions of the metallic layer are "lifted off", or removed, from the structure by soaking to remove the underlying photoresist.

The next step 518 in process 500 is to form metallic structures on a glass substrate. The result of this step is shown in FIG. 6E. As shown, metallic stripes 624 have been deposited onto a glass substrate 626. Stripes 624 form an optical grating used to sense position of the moving member. One good choice of material for glass substrate 626 is #7740 (Pyrex) glass, which is commercially available from Corning of Corning, N.Y. This material is advantageously able to form a strong anodic bond with silicon. Metallic stripes 624 may be formed on substrate 626 by using a similar "lift off" method that was discussed above in connection with step 516.

The next step 520 in process 500 is to invert the structure produced at the end of step 516 (i.e., and shown in FIG. 6D) and bond it to the structure produced at the end of step 518 (i.e., and shown in FIG. 6E). The result of this step is shown in FIG. 6F. As shown, the raised silicon portions 618 are bonded to the upper surface of glass substrate 626. At the conclusion of this step, the optical grating 622 formed on structure 620 is generally opposite to the optical grating 624 formed on substrate 626. The raised silicon portions 618 may be bonded to the glass substrate 626 by heating the structures to 180–500 degrees Celsius and applying a potential of 200–1000 Volts across the bond area. Under these conditions, a strong bond is achieved in about ten minutes.

The next step 522 in process 500 is to remove the "handle wafer" from the SOI structure. The result of this process is shown in FIG. 6G. As shown, the handle wafer 612 has been removed from the dielectric layer 614. Various methods can be used to remove the handle wafer 612 such as liquid etching, plasma etching, or etching with a gaseous silicon etchant such as xenon fluoride (XeF2).

The next step 524 in process 500 is to remove the dielectric layer 614 from what remains of the SOI wafer. The result of this step is shown in FIG. 6H. The dielectric layer 614 may be removed by plasma etching. At this point, structure 620 has been freed for movement and may now act as the central moving member (e.g., as shown at 132 in FIG. 2B) of a resonant sensor. FIG. 6I shows a view of this structure taken in the direction of the arrow 6I—6I as shown in FIG. 6H. As shown, the structure 620 is connected to the anchors by tethers as in the sensor shown in FIG. 2B. The tethers shown in FIG. 6I were defined by protecting the silicon material forming the tethers from the etch step performed at step 514.

Figure 6J:
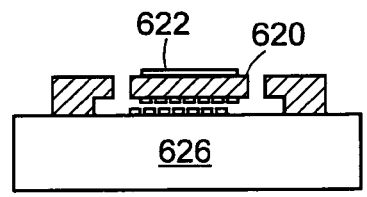
Figure 6E:
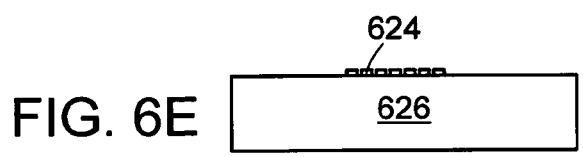
Figure 6F:
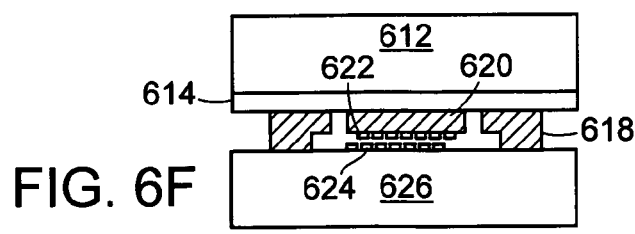
Figure 6G:
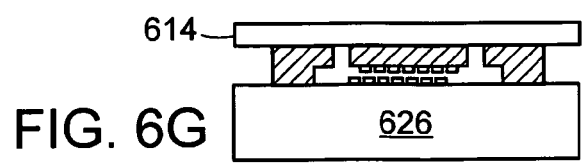

The next step 526 in process 500 is to form the receptor area 622 on the moving member 620, as shown in FIG. 6J. The process of forming the receptor area 622 will be discussed further below. However, it may include depositing layers of titanium and gold on the moving member structure 620. Gold is useful for forming receptor sites and titanium is useful for binding gold to the silicon structure 622.

Although the steps of process 500 have been discussed in connection with forming a single sensor chip, which has a single resonant sensor on it, it will be appreciated that process 500 may be used to form a plurality of sensor chips, and each of the chips may include a plurality of resonant sensors. After wafer processing has been completed, the wafer is diced up into individual chips, typically by using a die saw. Moving microstructures are preferably protected during wafer dicing. A layer of photoresist that is subsequently removed is generally adequate for this purpose.

Figure 7A:
FIGS. 7A–7G show products produced at various stages of another embodiment of a process for forming a sensor chip according to the invention.

FIGS. 7A–7G illustrate intermediate products produced at various states of an alternative process for forming a sensor chip 120. This process may be referred to as a "dissolved wafer process". As shown in FIG. 7A, the process begins by obtaining a silicon wafer. Unlike process 500, an SOI wafer is not used in the dissolved wafer process.

Figure 7B:
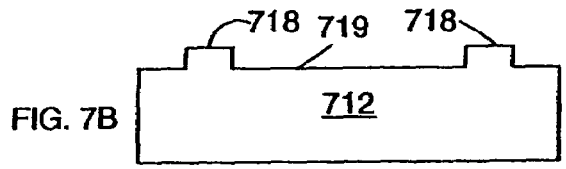
Figure 7C:
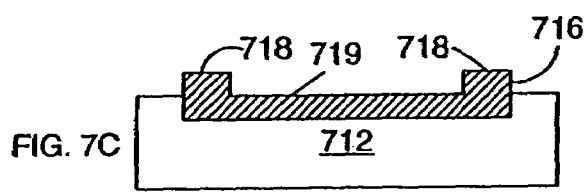

As shown in FIG. 7B, the upper surface of the wafer is then etched to produce raised areas 718 that stand above a lower surface 719. The geometric configuration and dimensions of the raised areas 718 are similar to those of the raised areas 618 shown in FIG. 6B, and the raised areas 718 will later form the anchors of the resonant sensor. As shown in FIG. 7C, a structural layer 716 is then defined by implanting portions of the wafer between the raised areas 718 with Boron.

Figure 7D:
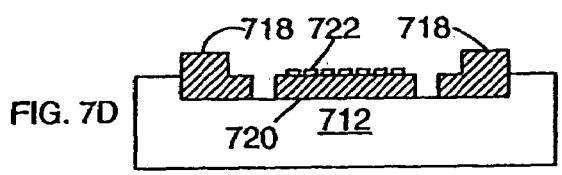

As shown in FIG. 7D, portions of structural layer 716 are then etched to define structure 720. After additional processing, structure 720 will form the central moving member of a resonant sensor. The tethers that connect the anchors to the central moving member are also defined by this etch. FIG. 6I, which shows the tethers, shows a top view of the general appearance of the structure shown in FIG. 7D. As shown in FIG. 7D, metallic stripes 722, which form an optical grating, are also formed on top of structure 720.

Figure 7E:
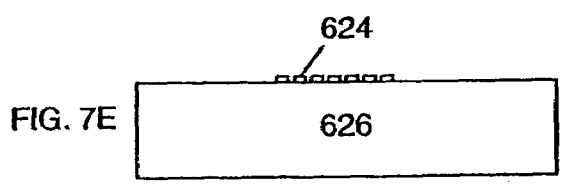

As shown in FIG. 7E, metallic stripes 624, which form an optical grating, are formed on a glass substrate. This step is identical to step 518 of process 500.

Figure 7F:
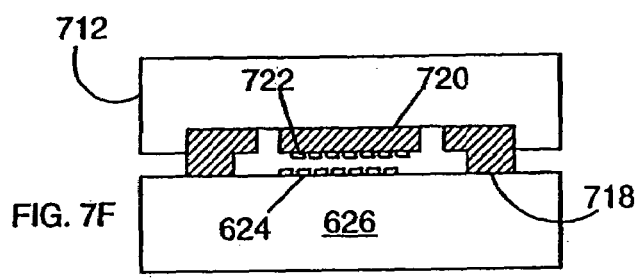

The structure shown in FIG. 7D is then inverted and bonded to the structure shown in FIG. 7E. This bonding may be accomplished as discussed in connection with step 520 of process 500. FIG. 7F shows the structure formed after this bonding step.

Figure 7G:
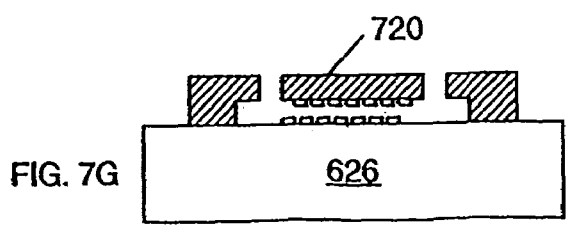

As shown in FIG. 7G, the portions of wafer 712 that were not implanted with Boron are then dissolved. A selective etchant such as ethylene diamine pyrocatechol (EDP) can be used for this purpose (as is described, e.g., in Gianchandani, Y. B. and Najafi, K., "A bulk silicon dissolved wafer process for microelectromechanical devices," J. MEMS, Vol. 1, No. 2, 1992.). Although they are produced by different processes, the structures shown in FIGS. 7G and 6H are similar. Fabrication may be completed by forming the receptor area on the structure 720 and then dicing the wafer to form individual sensor chips.

FIGS. 8A–8F illustrate intermediate products produced at various states of another alternative process for forming a sensor chip 120. As shown in FIG. 8A, processing begins by obtaining a silicon wafer 812.

As shown in FIG. 8B, a sacrificial layer 850 is then formed over substrate 812. Sacrificial layer 850 may be formed for example from silicon dioxide.

As shown in FIG. 8C, holes 852 are then etched through selected portions of layer 850. An additional etch process can be added here to form depressions in the silicon dioxide in the region corresponding to the position of the subsequently formed central moving member. A timed etch using hydrofluoric acid can be used for this process. When the structural layer is deposited conformally on top of the sacrificial layer, protrusions are formed to prevent stiction after release.

As shown in FIG. 8D, a silicon layer 860 is then formed over sacrificial layer 850. Layer 860 is formed such that the deposited silicon fills the holes 852 that were previously etched in layer 850. The deposited silicon also fills any depressions previously formed in sacrificial layer 850 by the additional etch process discussed above in connection with FIG. 8C. After additional processing, the silicon that filled holes 852 will form the anchors of the resonant sensor.

As shown in FIG. 8E, metal 870 is then formed over silicon layer 860. After additional processing, metal 870 will form a portion of the receptor area of the resonant sensor.

As shown in FIG. 8F, portions of silicon layer 860 are then etched to define the moving member 860 (and tethers) and expose portions of the sacrificial layer 850. The sacrificial layer is removed by a subsequent etch step to release the moving member (e.g., etching of silicon dioxide using hydrofluoric acid). Holes can be etched into the central moving member to reduce the time required for the release process. These can be made small enough and well spaced as to not interfere with the optical transduction process. This etch step produces the moving member as well as tethers (not shown) connecting the moving member to the anchors 890. Again, although they are produced by different processes, the structures shown in FIGS. 6J and 8F are similar. However, unlike the structure shown in FIG. 6J, the structure shown in FIG. 8F does not include an optical grating that may be used for sensing the position of the moving member. Other sensing schemes, which are discussed below, may be used to sense the position of the moving member 880.

It is also possible to fabricate the moving member, anchors, and tethers from a metal, such as, nickel, iron, iron-nickel alloys, copper or gold. Plating processes are advantageous for forming these structures since the metal layers produced tend to have low stress levels and predictable properties. The fabrication process starts with a planar substrate, such as a silicon, ceramic (e.g., aluminum nitride) or glass (e.g., Pyrex) wafer. A thin conductive seed layer is deposited on the substrate. For example, 500 Angstroms of chromium followed by 2000 Angstroms of gold is adequate. Other metal layer combinations and thicknesses can be used. Additionally, the layer can be patterned using standard photolithographic methods if desired. A layer of photoactivated polymer (e.g., photoresist, polyimide) is then deposited over the seed layer and then patterned to define the locations of the anchors. A metal, such as nickel, is then formed by electroplating so as to fill the holes defined by the patterned photoresist with metal. This metal is formed to the desired thickness to define the height of the anchors and accordingly the gap between the moving member and the substrate. This thickness matches approximately the height of the polymer layer. Subsequently, the metal anchors and polymer can be planarized if desired. A second seed layer of metal is then formed over the anchors and polymer photoresist. This second seed layer is then patterned to define the shape of the tethers and the central moving member. A second layer of polymer photoresist is then deposited over this second seed layer. The second layer of photoresist is then patterned to expose the second seed layer (i.e., to expose the sites where the tethers and moving member will be formed). The second layer of patterned photoresist effectively acts as a mold for forming the tethers and moving member. Electroplating is then used to from a thicker metal layer over the second seed layer. This thicker metal layer forms the tethers and the central moving member. The plating time is controlled to insure that the tethers and central moving member have the desired thickness. The top surface can be planarized to reduce the surface roughness if desired. A final metal layer (e.g., gold) can patterned on top of the central moving member for attachment of receptors and/or to facilitate optical sensing, as described in for previous fabrication methods. A solvent is then used to remove the photoresist and release the metallic central moving member for movement with respect to the substrate.

The process described here for producing a moving member constructed from metal is only one example. More advanced plating methods include LIGA processing as well as the Efab process available from MEMGen, Burbank, Calif.

As discussed above in connection with FIG. 1A, optical system 180 monitors the resonant sensors 130 on the sensing chip 120. More particularly, optical system 180 monitors the instantaneous position of the central moving member of the resonant sensors. Measuring the instantaneous position over time allows the measurement system to determine the oscillation frequencies of the moving members. Measuring the instantaneous position of the central moving member over time also allows the sensing system to determine other characteristics of the moving member, such as the dissipation or the rate at which the oscillatory motion is damped.

Other, non-optical, approaches have been used in the prior art to monitor the position of a moving member in a MEMS device, such as capacitive, piezoresistive, and piezoelectric methods. These methods can be employed in the current invention. However, optical monitoring is advantageously unaffected by the presence of a conducting solution (e.g., salts in the sample).

As shown in FIGS. 2A, 6J, and 7G, the resonant sensors may be fabricated so as to include two oppositely disposed optical gratings (i.e., one grating disposed on the central moving member and another grating disposed on the underlying substrate). The optical gratings allow the optical system 180 to monitor the instantaneous position of the central moving member of the resonant sensor 130. More specifically, in operation light source 182 emits a continuous narrow band beam of light that is incident on the optical gratings of a resonant sensor. Structures (e.g., such as the substrate or mount) disposed between the light source 182 and the resonant sensor are preferably transparent to the wavelengths emitted by the source 182. Light diffracted from the gratings is received by detector 184. Using well known optical techniques, the intensity distribution in the diffracted field received by detector 184 may be used to determine the position of the moving member of the resonant sensor 130. Optical system 184 is generally capable of detecting motions of the central moving member that are as small as one Angstrom, or less, when the moving member is oscillating at frequencies of about one MHz.

FIG. 2C shows the stripes of the grating 142 being oriented at forty five degrees relative to the X and Y axes. In this configuration, equal displacements of the moving member in the X and Y directions produce the same change in relative position of the two optical gratings (e.g., gratings 142 and 144 as shown in FIG. 2A). Thus, a single grating can be used to transduce both motions. Since the resonant frequencies of the two modes differ, electronic filtering or signal processing methods (e.g., Fourier decomposition) can be used decompose the electrical signal from the photodetector into the two components.

FIG. 9A illustrates an alternative structure for optically monitoring the moving element of a resonant sensor. The sensor 900 shown in FIG. 9A is similar to the structure shown in FIG. 8F. However, the sensor 900 additionally includes two photodiodes 910 that have been formed in the silicon substrate 812. Methods for forming such photodiodes are well known and are described for example in Padmanabhan, A., Goldberg, H., Breuer, K. D., and Schmidt, M. A., "A wafer-bonded floating-element shear stress microsensor with optical position sensing photodiodes," J. MEMS, Vol. 5, No. 4, 1996. The process for forming sensor 900 is similar to the process described in connection with FIGS. 8A–8F, however, the photodiodes are formed prior to forming the sacrificial layer 850.

In operation, sensor 900 is illuminated from above and photodiodes receive light that passes through apertures 902 between the moving member and the anchors. As the moving member moves, the sizes of apertures 902 change thereby increasing or reducing the amount of light incident on the photodiodes. The photodiodes generate output signals representative of the amount of light incident on the photodiodes. The output signals generated by the photodiodes are accordingly indicative of the instantaneous position of the moving member 880. Monitoring these signals over time allows the measurement system to measure the oscillation frequency of the moving member.

In one embodiment, the width of the apertures 902 is nominally (i.e., when the moving member is stationary) five microns. In this embodiment, displacement of the moving member by one nanometer changes the size of the apertures 902 by 0.02%. The output signals generated by the photodiodes are generally out of phase and can be detected differentially to improve the signal-to-noise ratio. Photodiodes configured as shown in FIG. 9A are generally able to detect displacements of the central moving member that are less than one nanometer.

FIG. 9B illustrates another structure in which photodiodes may be used to monitor the oscillation frequency of the central moving member of a resonant sensor. As shown in FIG. 9B, the central member 880 is supported by tethers that are fixed to the substrate at anchors 890. Stationary masks 882 generally surround the moving member 880. Four photodiodes, designated A, B, C, and D are disposed around the corners of the moving element 880. Light passing through the apertures between the moving member 880 and the stationary masks 882 is received by the photodiodes. Photodiode A is positioned slightly above and to the left of the southwest corner (or lower left corner) of the moving member 880; photodiode D is positioned slightly to the right of and below the southwest corner; photodiode C is positioned slightly above and to the left of the northeast corner (or upper right corner) of the moving member; and photodiode B is positioned slightly below and to the right of the northeast corner.

The output signals generated by the four photodiodes may be combined in various ways to produce signals indicative of position of the moving member 880 in the X, Y, and theta directions. In general, the difference of the output signals generated by photodiodes A and B is indicative of position of moving member 880 as measured in the X direction (i.e., X position indicated by A–B); and the difference between the output signals generated by photodiodes C and D is indicative of the position of the moving member as measured in the Y direction (i.e., Y position indicated by D–C). Finally, the difference between the sum of the output signals generated by photodiodes C and D and the sum of the output signals generated by the photodiodes A and B is indicative of the rotational orientation of the moving member 880 (i.e., Rotation position indicated by (A+B)–(C+D)). Monitoring these signals over time provides measurement of the oscillation frequencies of the moving member 880 in the X, Y, and theta directions.

The structure shown in FIG. 9B may be fabricated using a process similar to that used to produce sensor 900 (shown in FIG. 9A). However, the stationary masks 882 must also be formed. Stationary masks 882 may be formed by covering these areas with photoresist to protect them during the etch step used to define the moving member. Additionally, the lateral extent of these areas is such that they are not completely undercut during the release process, maintaining their structural integrity.

Another alternative approach for optically monitoring the position and oscillation frequency of the central moving member of a resonant sensor is to illuminate the sensor with a pulsed source (or strobed source) and to image light reflected from the moving member with a phase-locked imaging system. The light pulses are of a duration sufficiently short to effectively freeze the motion of the central moving member. Several images recorded at the same phase can be averaged to reduce noise. For moving members that have an amplitude of about ten nanometers and a frequency of about one MHz, a pulse duration of about ten nanoseconds is used to resolve a one nanometer displacement of the moving member. This is achievable with a variety of laser sources (e.g., visible semiconductor lasers). The reflected light can be imaged onto a CCD camera. Imaging systems based on this approach are commercially available, for example, the MMA G2™ MEMS Motion Analyzer from UMech Technologies of Watertown, Mass. Reflective features can be included on the moving and stationary portions of the sensor chip to facilitate referenced displacement measurements. This facilitates rejecting bulk movement of the assembly relative to the imaging system.

Figure 10A:
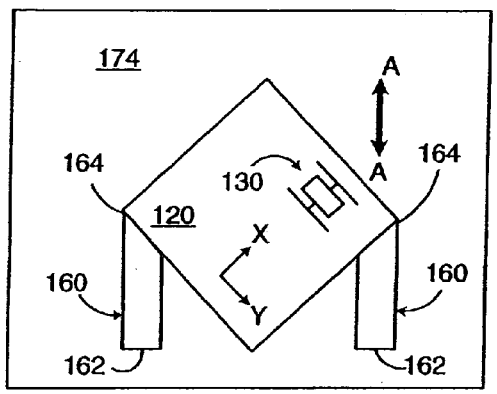
FIGS. 10A, 10B, and 10C show embodiments for actuating a sensor chip according to the invention.
Figure 10B:
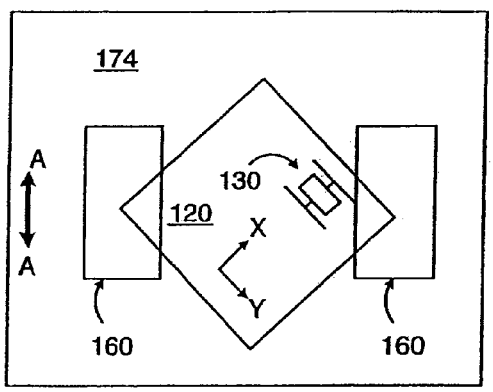
Figure 10C:
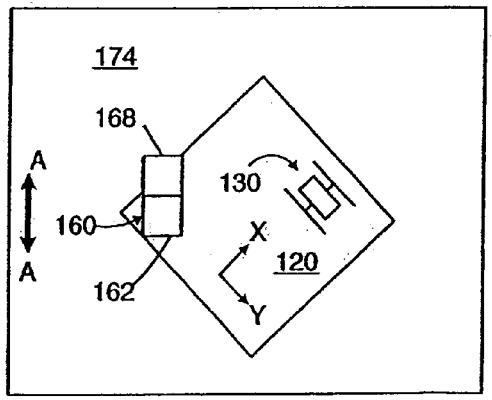

FIGS. 1A and 1B show sensor chip 120 mounted on an actuator 160 and an anchor 178. As discussed above, actuator 160 can move sensor chip 120 by controlled minute amounts to excite oscillatory motion of the resonant sensors 130. FIGS. 10A, 10B, and 10C show alternative configurations of actuators 160 for selectively moving sensor chip 120. In each configuration, the actuators 160 may be implemented using piezoelectric devices that produce motion in response to electrical stimulus. Preferred piezoelectric devices are excited by an electrical stimulus on the order of one to ten Volts and produce controlled motions of approximately one to ten nanometers over a bandwidth of about 0.1 to tens of MHz. It may be desirable to use hard composition (e.g., material designation PZT-4, Morgan Electroceramics, Ruabon, Wrexham, UK) material to form the actuators 160 so that they dissipate minimal internal power. In FIG. 10A, the sensor chip 120 and two actuators 160 rest on a substrate (e.g., such as the lower surface of the well 174 defined in the mount 172, which is shown in FIG. 1A). One end 162 of each actuator 160 is fixed to the substrate. The other end 164 of each actuator 160 is fixed to a corner of the sensor chip 120. When activated, the end 164 of an actuator 160 may be moved up or down (in the direction indicated by the arrow A—A) with respect to the anchored end 162 so as to move the sensor chip in a controlled fashion. The two actuators 160 may be activated in phase, or out of phase (i.e., such that the end 164 of one actuator 162 moves up as the end 162 of the other actuator moves down).

In FIG. 10B, two actuators 160 are mounted to a substrate and the sensor chip 120 is mounted to the tops of the actuators (i.e., similar to the configuration shown in FIG. 1A). In FIG. 10C, the sensor chip 120 is mounted on a substrate and one end 162 of the actuator 160 is mounted to the top of the sensor chip 120. A mass 168 is attached to one end of the actuator 160. Actuation of actuator 160 moves the mass 168 up and down (in the direction indicated by the arrow A—A), and thereby excites motion of the sensor chip 120.

Regardless of which configuration is used, the actuators may excite (or move) the sensor chip over a frequency range of about 0.1–10 MHz. The inertia of the central moving members of the resonant sensors causes excitation of the resonant sensors when the substrate of the sensor chip 120 is excited (or moved).

It may be advantageous to encapsulate the substrate of the sensor chip 120 and the actuator(s) 160 in a compliant sealant. Such encapsulation may protect the electrical drive of the actuator from exposure to a liquid/fluid sample.

In all of the configurations discussed above, motion of the substrate of the sensor chip 120 simultaneously excites all of the resonant sensors. This implementation has several benefits (i.e., as opposed to independently moving each of the resonant sensors). First, each resonant sensor is excited by a like source so that systematic influences of excitation authority and phase lags are common to all measured resonant sensor responses. As a result, comparison of responses of the resonant sensors is more accurate. Second, the excitation source is isolated from the resonant sensors, thereby eliminating potential sources of electrical cross talk and noise. Also, when driving large arrays of resonant sensors, the use of a limited number of excitation sources greatly reduces the overhead of routing power carrying electrical connections.

FIG. 1A shows a sensing system 100 that defines a sample inlet 110, a sample outlet 112, and a channel 111 for allowing a liquid or gas sample to be exposed to the sensor chip 120. In operation, the sensor chip 120 may be exposed to a set of different samples by sequentially flowing one sample after another through the channel 111.

It may be useful to fabricate sensor chips such that the receptor areas on every resonant sensor on the chip selectively bind to the same measurand. Such sensor chips can enhance accuracy by providing redundant measurements. Alternatively, it may also be useful to fabricate sensor chips in which each resonant sensor is used to detect the presence of a unique measurand. In such sensor chips, the receptor area on each resonant sensor selectively binds to a particular measurand that is different than the measurands detected by the other resonant sensors. If such a sensor chip has n resonant sensors, where n is an integer (e.g., n=20), the chip can be used to detect the presence of n different measurands in a sample or series of samples. As yet another alternative, sensor chips may be constructed according to the invention that have n resonant sensors and that are used to detect the presence of m different measurands, where m is an integer less than n. In such sensor chips, two or more resonant sensors may be devoted to detecting a particular measurand. Also, some of the resonant sensors on the chip may be control sensors that are never exposed to a sample. Such a control sensor may be produced by placing a covering over the sensor that prevents the sensor from being exposed to the sample and yet allows other resonant sensors on the chip to be exposed to the sample. Such control sensors may be used to provide a reference for calibrating other sensors on the chip and for compensating for environmental factors. Such a covering 101, for protecting two of the resonant sensors 130 from the sample, is shown in FIG. 1A.

In some environments it may be necessary to couple the inlet 110 and the outlet 112 to sample sources and waste disposals, respectively, via piping or conduits. It may be advantageous to use conduits made from compliant material (such as PDMS, which is commercially available from Dow Corning, Midland, Mich.) to minimize mechanical coupling between the sensor chip and the sample source.

FIG. 1A shows the optical system 180 sensing the position of the resonant sensors from below. However, in an alternate configuration, the optical system 180 may be disposed above the mechanical system 105. In such configurations it may be desirable to fabricate cover 179 from an optically transmissive material or to eliminate the cover 179. An example of an optical system that can be disposed above the mechanical system is the phase-locked imaging system discussed above.

Figure 11A:
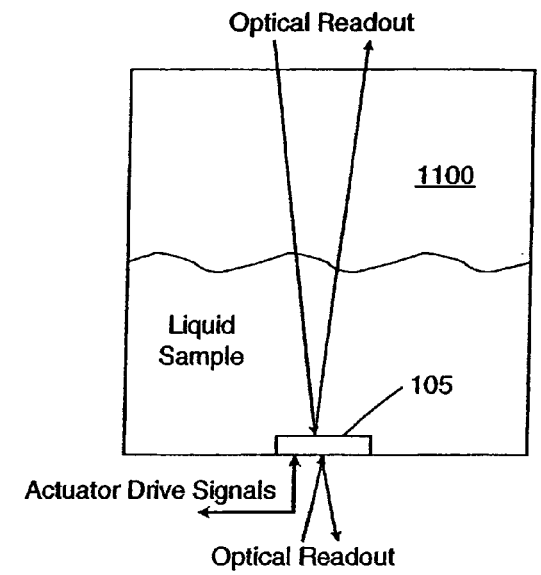
FIG. 11A shows a mechanical system constructed according to the invention installed in the base of a reservoir and operating in a liquid environment.
Figure 11B:
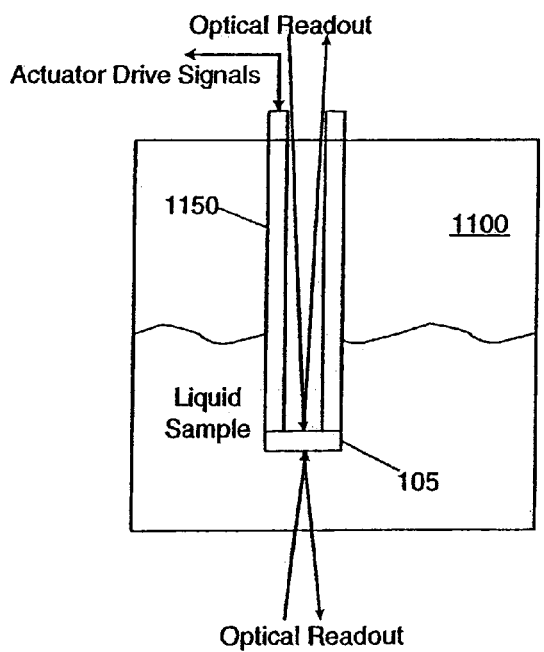
FIG. 11B shows a mechanical system constructed according to the invention installed in a movable probe tip and operating in a liquid environment.

FIGS. 11A and 11B illustrate alternative configurations for exposing the sensor chip to a liquid sample. In FIG. 11A, the mechanical system 105 is disposed at the bottom of a reservoir 1100 of liquid sample. Reservoir 1100 may be, for example, one well of a 96-well or 384-well plate of the type normally used for bioassays. The mechanical system 105 used in a configuration of the type shown in FIG. 11A would normally include a sensor chip 120, one or more actuators 160 and a substrate. Since the sensor chip is submerged in the liquid sample, the cover 179 (shown in FIG. 1A) would normally not be used. Also, the mount 172 (shown in FIG. 1A) may be eliminated and the sensor chip 120 and actuator(s) may be mounted directly to a substrate. As shown in FIG. 11A, electrical connections for supplying power and control to the actuator(s) 160 may be provided through the bottom of reservoir 1100. The electrical connections may be provided using either standard lead-type connections or spring-loaded pins contacting pads. Spring-loaded pins advantageously facilitate rapid replacement of the well plate reservoirs. Optical access to the sensor chip for monitoring the resonant sensors may be provided from below or above as indicated in FIG. 11A. However, it may be advantageous to optically monitor the resonant sensors from below so that the light need not propagate through the liquid sample.

FIG. 11B shows a configuration in which the mechanical system 105 is part of a probe 150, the distal tip of which is submerged in a liquid sample. The mechanical system 105 for use in the FIG. 11B is similar to the one discussed above in connection with FIG. 11A except that it is mounted to the probe 1150. In this configuration, electrical signals for actuating and controlling the actuator(s) 160 are supplied via the probe 1150. The orientation of the sensor chip is preferably such that the resonant sensors 130 (not shown in FIG. 11B) are near the bottom surface of mechanical system 105 (i.e., the sensor chip is inverted as compared with the orientation shown in FIG. 1A and 1B). Again, the optical readout may be from above or below, although in this case, optical access from above advantageously prevents the light from propagating through the sample.

Figure 13:
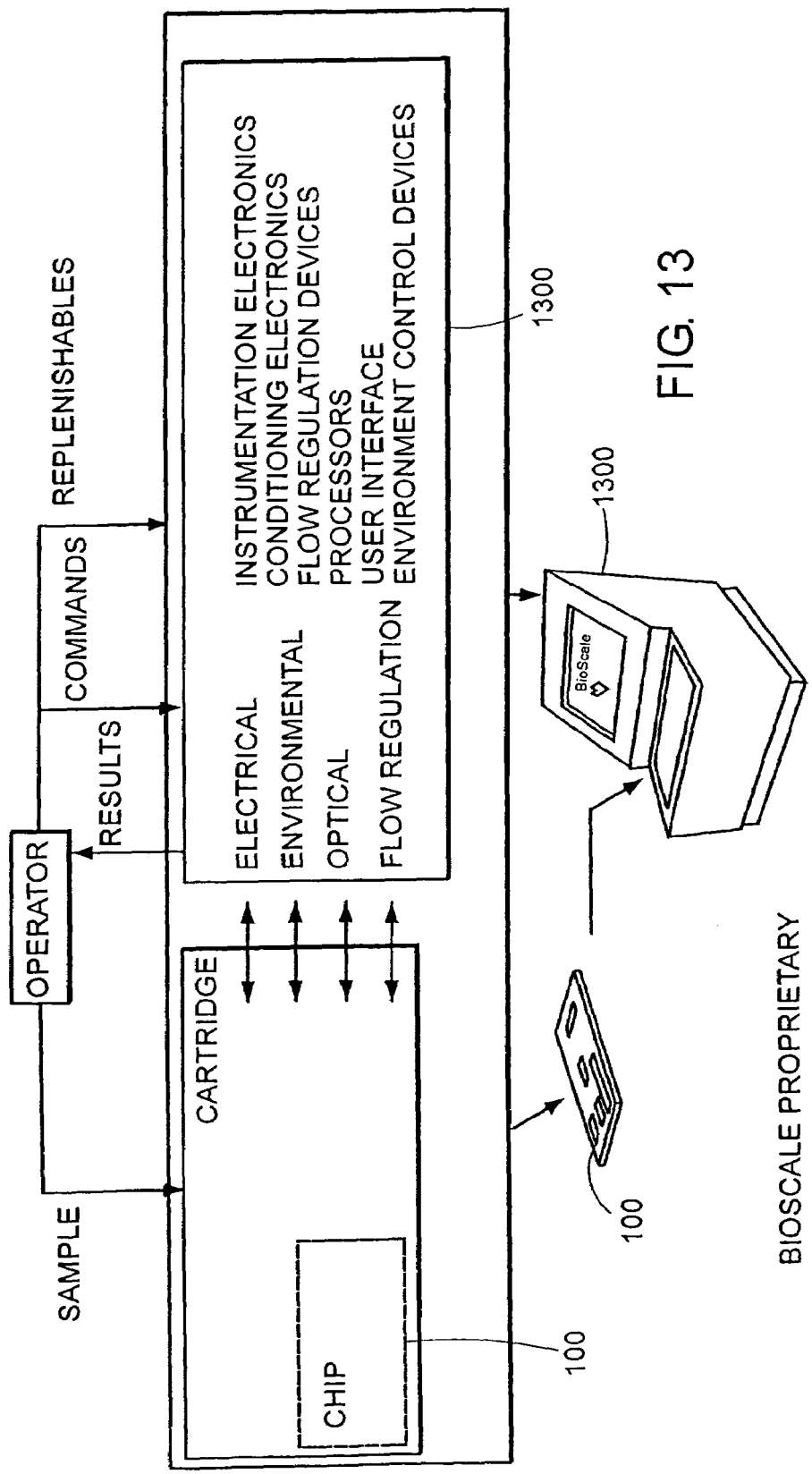
FIG. 13 shows an instrument used for controlling and monitoring a sensing system.

FIG. 13 shows a sensing system 100 integrated with an instrument 1300 for controlling the sensing system and for interpreting the results of experiments performed with the sensing system. The instrument 1300 provides electrical signals to system 100 for, for example, controlling oscillation of the substrate in system 100 and the instrument receives electrical signals produced by sensing system for monitoring the motions of the resonant sensors (e.g., signals produced by the optical system). Instrument 1300 also includes a data processor for analyzing the signals received from sensing system 100 as well as controllers for selectively exposing the sensing system 100 to a sample.

The resonant sensor can be used in a variety of applications, including those normally associated with other acoustic or resonant sensors. Particularly useful applications fall into three main categories: (1) fluid characterization; (2) small chemical species detection; and (3) biological analyte detection. A review of the various sensor applications for traditional resonant or acoustic sensors (e.g., quartz crystal microbalances and surface acoustic waves devices) can be found in Balantine et al., *Acoustic Wave Sensors: Theory, Design, and Physico-Chemical Applications*, Academic Press, San Diego, 1997. The nature of the preparation of the receptor area depends on the application for which the resonant sensor is intended. For sensing physical properties of fluids (e.g., viscosity or density of liquids) no additional processing may be required. For detection of chemical species or biological analytes, however, the surface treatment will depend on the specific measurand to be monitored.

Thus, in some embodiments, the resonant sensor is used for fluid characterization to measure the density or viscosity of a gas or liquid. Similarly, the viscoelastic properties of gels and polymers can be measured. In these applications, no specific receptor molecules need to be bound to the receptor area of the sensor. Rather, the non-specific physical interaction of the fluid with the receptor area can have a detectable effect on the moving member.

In other embodiments, the resonant sensor is used for detecting chemical species present in fluids such as vapors, gases, or liquid solutions. In these embodiments, an adsorbent layer can be applied to the sensor surface which adsorbs the measurand to be detected. The adsorbent layer can be a thin polymer layer, the properties of which can vary with the nature and the amount of the measurand to be adsorbed. For example, the adsorbent layer can be chemically reactive with the measurand such that the measurand becomes covalently bound to the layer. Alternatively, the adsorbent layer can adsorb the measurand through non-covalent interactions (e.g., electrostatically or through hydrophobic or hydrophilic interactions). As a result of adsorbing the measurand, the mass of the moving member will be changed and, therefore, its resonant characteristics will be affected.

A large variety of chemical species can be sensed by employing thin layers of polymers that adsorb the measurand. Families of such chemo-selective polymers have been developed for detecting different classes of chemical vapors, including hydrocarbons, chemical warfare agents and explosives (e.g., McGill et al., "Choosing Polymer Coatings for Chemical Sensors," Chemtech, 1994, p. 27; Houser et al., "Rational Materials Design of Sorbent Coatings for Explosives: Applications With Chemical Sensors," Talanta, 54 (2001), pp. 469–485. Polymer layer thicknesses typically range from between 10 nm–1 µm. In order to deposit the layer, the polymer can be dissolved in a solvent, sprayed on the surface and allowed to dry or, in some embodiments, laser deposition techniques can be employed. A mask can be used to confine the coating to all or some of the receptor area.

Alternatively, the resonant sensor can be used to detect chemical species which react with the receptor area by, for example, causing oxidation, reduction, dissolution, or corrosion of a chemical or material deposited onto the receptor area. For example, the presence and concentration of corrosive vapors can be detected by coating the surface with a material known to react with vapors of interest. Metals are commonly used, and most can be evaporated or sputtered onto the surface as a thin film, using a mask to confine the coating to specific areas of the sensor. For example, and without limitation, a layer of copper or silver can be used to detect the presence of hydrogen sulfide ($H_2S$). Alternatively, the sensor can be used to evaluate the corrosion resistance of materials. For example, the sensor can be coated with the material of interest and the change in signal monitored during exposure to a known amount of corrosive vapor. Studies in liquid environments are also possible. By reacting with the polymer layer, the measurand can alter the mass of the moving member without being adsorbed thereto.

Chemical interactions with the polymer also can alter properties of the layer other than mass (e.g., viscoelastic properties, internal strain) and these can be detected in conjunction with or independently of the mass change. Moreover, the resonant sensor can be designed such that the altered properties result in a change in the resonant characteristics. For example, the tethers can be coated with the polymer, or the structure can be designed so that stresses induced in the central element are transferred to the tethers.

The resonant sensors of the invention can also be used to detect biological measurands, for example, whole cells (e.g., bacteria, yeast, fungi, blood cells, dissociated tissue cells), spores (e.g., fungal or yeast), viruses (e.g., HIV), proteins (e.g., growth factors, cytokines, and prions), lipids (e.g., cholesterol), carbohydrates (e.g., sugars, glycosaminoglycans, lipopolysaccharides), nucleic acids (e.g., DNA or RNA), and various small molecules (e.g., hormones, pharmaceutical drugs). Such biosensor devices are useful in a wide array of applications, including cytometry, toxicology, diagnostics, genomic profiling and forensic identification.

Detection of such biological measurands requires immobilizing a receptor molecule on the receptor area which is specific for the measurand. Generally, the goal is to maximize the specificity of binding for the target while minimizing non-specific binding of other molecules (e.g., interferents). In many cases, complete specificity will be unachievable and, in some cases, it will be unnecessary. Rather, the degree of specificity required will depend upon the relative amounts of the measurand and interferents in the sample, as well as the ability to distinguish amongst them by other means. In some embodiments, the measurands will be a class of molecules and, therefore, specificity for the class will be desirable whereas specificity for molecules within the class will not.

The receptor molecules useful in specific embodiments will depend upon the nature of the measurand. Useful receptor molecules include antibodies, polynucleotides, aptamers, cell surface receptors, cytoplasmic receptors, binding domains, small molecule ligands, sugars, polysaccharides, glycans, glycoproteins and the like.

For example, antibodies can be used as receptors in the resonant sensors of the invention. As used herein, the term "antibody" is intended to embrace naturally produced antibodies, recombinantly produced antibodies, monoclonal antibodies, and polyclonal antibodies, as well as antibody fragments such as Fab fragments, $F(ab')_2$ fragments, Fv fragments, and single-chain Fv fragment (scFv). Useful antibody receptors include all immunoglobulin classes, such as IgM, IgG, IgD, IgE, IgA and their subclasses. Antibodies may be produced by standard methods, well known in the art. See, e.g., Pluckthun, Nature 347:497–498 (1990); Huse et al., Science 246:1275–1289 (1989); Chaudhary et al., Proc. Natl. Acad. Sci. USA 87:1066–1070 (1990); Mullinax et al., Proc. Natl. Acad. Sci. USA 87:8095–8099 (1990); Berg et al., Proc. Natl. Acad. Sci. USA 88:4723–4727 (1991); Wood et al., J. Immunol. 145:3011–3016 (1990); and references cited therein. Antibody receptors are particularly useful for capturing measurands such as whole cells (e.g., cells bearing a cell surface molecule which binds the antibody), spores (e.g., fungal or yeast), viruses (e.g., HIV), and proteins (e.g., growth factors, cytokines, and prions).

Polynucleotides are also useful as receptor molecules in the present invention. As used herein, the term "polynucleotide" means any molecule comprising a sequence of covalently joined nucleoside-like chemical units which has selective binding affinity for a naturally-occurring nucleic acid of complementary or substantially complementary sequence under appropriate conditions (e.g., pH, temperature, solvent, ionic strength, electric field strength). Polynucleotides include naturally-occurring nucleic acids as well as nucleic acid analogues with modified nucleosides or internucleoside linkages, and molecules which have been modified with linkers or detectable labels which facilitate immobilization on a substrate or which facilitate detection.

The polynucleotide receptors can be DNA molecules, RNA molecules, or polynucleotides having modified nucleoside bases or modified internucleoside linkages. Useful modifications include, but are not limited to, those which provide other chemical groups that incorporate additional charge, polarizability, hydrophobicity, hydrogen bonding, or electrostatic interaction.

Examples of modified nucleoside bases include, without limitation, the modified bases described in WIPO Standard ST.25 (1998), Appendix 2, Table 2, the entire disclosure of which is incorporated by reference herein (see also 37 C.F.R. 1.821–1.825). Examples of nucleoside base modifications include, without limitation, 5-position pyrimidine modifications, 8-position purine modifications, modifications at exocyclic amines, and the like. Specific modifications include, without limitation, modified cytosine bases including isocytosine, 5-methylcytosine, 4-acetylcytosine, 3-methylcytosine, 5-hydroxymethyl cytosine, 2-thiocytosine, 5-halocytosine, 5-propynyl cytosine, 6-azocytosine, 5-trifluoromethylcytosine, N4, N4-ethanocytosine, phenoxazine cytidine, phenothiazine cytidine, carbazole cytidine or pyridoindole cytidine; modified guanine bases including isoguanidine, 6-methylguanine, 1-methylguanine, 2,2-dimethylguanine, 2-methylguanine, 7-methylguanine, 2-propylguanine, 6-propylguanine, 8-haloguanine, 8-aminoguanine, 8-sulflhydrylguanine, 8-thioalkylguanine, 8-hydroxyguanine, 7-methylguanine, 8-azaguanine, 7-deazaguanine or 3-deazaguanine; modified adenine bases including 6-methyladenine, N6-isopentenyladenine, N6-methyladenine, 1-methyladenine, 2-methyladenine, 2-methylthio-N6-isopentenyladenine, 8-haloadenine, 8-aminoadenine, 8-sulfhydryladenine, 8-thioalkyladenine, 8-hydroxyladenine, 7-methyladenine, 2-haloadenine, 2-aminoadenine, 8-azaadenine, 7-deazaadenine or 3-deazaadenine; modified thymine bases including dihydrothymine, 1-methylpseudothymine, 2-thiothymine, 4-thiothymine, pseudothymine, 2-thiothymine, 3-(3-amino-3-N-2-carboxypropyl)thymine, 6-azothymine, or 4-thiothymine; and modified uracil bases including 5-halouracil, 5-(carboxyhydroxylmethyl)uracil, 5-carboxymethylaminomethyl-2-thiouracil, 5-carboxymethylaminomethyluracil, dihydrouracil, 1-methylpseudouracil, 5-methoxyaminomethyl-2-thiouracil, 5'-methoxycarbonylmethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid, pseudouracil, 5-methyl-2-thiouracil, 2-thiouracil, 3-(3-amino-3-N-2-carboxypropyl)uracil, 5-methylaminomethyluracil, 5-propynyl uracil, 6-azouracil, or 4-thiouracil. Also useful are the modified bases described in U.S. Pat. Nos. 3,687,808, 3,687,808, 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091, 5,614,617, 5,645,985, 5,830,653, 5,763,588, 6,005,096, and 5,681,941.

Examples of modified internucleoside linkages include, without limitation, modifications of the ribosyl or deoxyribosyl units such as halogenation, alkylation, alkoxylation and the like, modification or replacement of the phosphodiester linkages (e.g., substitution with phosphorothioates or alkyl phosphates), or modification or replacement of both the (deoxy)ribosyl and phosphate backbone (e.g., substitution with peptide nucleic acid (PNA) linkages). One or more of the termini of such polynucleotides also can be modified (e.g., 5' or 3' inverted residues or caps). Modified internucleoside linkages can be useful to protect against degradation by nucleases present in a sample. See, for example, Wetmur, $Crit. Rev. Biochem. Mol. Biol.$ 26:227–259 (1991); Moody et al., $Nucleic Acids Res.$ 17:4769–4782 (1989); Iyer et al., $J. Biol. Chem.$ 270:14712–14717 (1995); Nielsen et al., $Science$ 254:1497–1500 (1999); Ortigao et al., $Antisense Res. Devel.$ 2:129–146 (1992)); Sinha et al., $Nucleic Acids Res.$ 12:4539–4557 (1984)). Polynucleotides with naturally-occurring bases and linkages can be produced synthetically or by organisms (e.g., bacteria) genetically engineered to produce them as transcription products. Polynucleotides with modified bases and linkages can be produced synthetically.

Examples of modified internucleoside linkages known in the art include, without limitation, those having, e.g., 2' ribosyl substituents such as F, Cl, Br, CN, SH, $OCH_3$, $SCH_3$, OCN, $CF_3$, $OCF_3$, $SOCH_3$, $SO_2$, $CH_3$, $ONO_2$, $NO_2$, $N_3$, $NH_2$, $OCH_2CH_2OCH_3$, $O(CH_2)_2ON(CH_3)_2$, $OCH_2OCH_2N(CH_3)_2$, $O(C_{1-10}$ alkyl), $O(C_{2-10}$ alkenyl), $O(C_{2-10}$ alkynyl), $S(C_{1-10}$ alkyl), $S(C_{2-10}$ alkenyl), $S(C_{2-10}$ alkynyl), $NH(C_{1-10}$ alkyl), $NH(C_{2-10}$ alkenyl), $NH(C_{2-10}$ alkynyl), and O-alkyl-O-alkyl, $OCH_2CH_2CH_2NH_2$, $CH_2-CH=CH_2$, and $O-CH_2-CH=CH_2$. The 2'-substituent may be in the arabino (up) position or ribo (down) position.

In some embodiments, polynucleotide receptor molecules have a length of between 15 and 200 bases. In certain embodiments, the polynucleotide receptor molecules have a length between 15 and 50 bases, between 50 and 80 bases, between 80 and 110 bases, between 110 and 140 bases, between 140 and 170 bases, or between 170 and 200 bases. Substantially longer polynucleotides also can be used.

Polynucleotide receptor molecules can be directed to sequences known to include polymorphisms in a particular population, including single nucleotide polymorphisms, deletions or insertions, or regions of microsatellite instability. In particular, polynucleotide receptor molecules can be directed to allelic sequences known to include sites of deleterious mutations for purposes of genotyping, or can be directed to sequences characteristic of the genome of a particular species (e.g., a pathogen) for purposes of diagnosing disease or detecting contamination.

Receptor molecules useful in the invention also include aptamers or "nucleic acid ligands." As used herein, the term "aptamer" means any polynucleotide having selective binding affinity for a non-polynucleotide molecule via non-covalent physical interactions. An aptamer is a polynucleotide that binds to a ligand in a manner analogous to the binding of an antibody to its epitope.

The aptamer polynucleotide sequences can be developed and selected by methods well known in the art (see, e.g., Tuerk et al. (1990), $Science$ 249:5050; Joyce (1989), $Gene$ 82:83–87; Ellington et al. (1990), $Nature$ 346:818–822; Klug et al. (1994), $Mol. Biol. Reports$ 20:97–107), and can be used as receptor molecules against many kinds of analytes, including proteins, carbohydrates and small organic molecules. Aptamers can be produced by any known method of producing polynucleotides, and can include modified nucleoside bases or modified internucleoside linkages as discussed above with respect to polynucleotides. See also U.S. Pat. No. 5,660,985.

Other receptor molecules useful in the invention include cell surface receptors (e.g., immune system molecules such as MHC antigens, T cell receptors and CD antigens; protein and peptide hormone receptors such as the thyroid-stimulating hormone, luteinizing hormone, follicle-stimulating hormone, calcitonin, somatotropin, vasopressin, parathyroid hormone, insulin and glucagon receptors; catecholamine receptors such as the dopamine, epinephrine and norepinephrine receptors; eicosanoid receptors such as the prostaglandin receptors; folic acid receptors), cytoplasmic receptors (e.g., thyroid hormone receptor, peroxisome proliferator-activator receptors (PPARs), and steroid receptors such as the estrogen, androgen, mineralocortocoid and glucocorticoid receptors), binding domains (e.g., DNA, RNA, metal, glycosaminoglycan, ubiquitin, cofactor and other ligand binding domains of various proteins), small molecule ligands (e.g., nucleotide mono-, di- and triphosphates, combinatorial chemistry libraries, peptide libraries), sugars (e.g., lactose, trehalose, L-arabinose, D-maltose), polysaccharides (e.g., bacterial endotoxin, mannan, pullulan, amylopectin, dextran), glycans (e.g., glycosaminoglycans (GAGs), glycosylation structures), and glycoproteins (e.g., lectins).

Finally, for blocking sites, blocking molecules may be chosen from a wide variety of molecules which have low affinity for binding, adhering, or adsorbing biological materials. Such groups include, without limitation, polar but uncharged groups (e.g., polyethylene glycol (PEG)) and hydrophilic groups (e.g., mannitol). In the discussion below, blocking molecules will be treated as a subset of receptor molecules, and will not be discussed separately.

Receptor molecules can be bound or attached to the surface of the receptor area using standard chemistries for the reactive groups already present on the receptor molecules and receptor area, or after derivatizing the receptor molecules or receptor area to produce or introduce desired reactive groups.

As noted above, the receptor area is a portion of the central moving member which may be produced from silicon. The receptor area can, however, be derivatized by depositing layers of titanium and gold on the moving member structure. Alternatively, other metals or metal oxides can be sputtered onto the surface. Such metal surfaces can be further derivatized with adaptor molecules which facilitate attachment of the receptor molecules.

Adaptor molecules can include an alpha reactive group which binds to the receptor area surface and an omega reactive group which can be reacted with the receptor molecules. For example, thiols bind strongly to gold surfaces and therefore adaptor molecules with alpha thiol reactive groups can be used with gold-coated receptor areas. Similarly, siloxanes bind to silicon surfaces, and fatty acids have been shown to bind to metal oxides. Therefore, siloxanes and fatty acids can be used as alpha reactive groups with silicon and metal oxide surfaces, respectively. For blocking sites, an adaptor molecule can be used in which the omega group is not reactive and terminates in a polar uncharged group (e.g., polyethylene glycol (PEG)) or hydrophilic group (e.g., mannitol).

Omega reactive groups for adaptor molecules can be chosen to complement the reactive groups available on the receptor molecules. For example, carboxyl groups can be reacted with amine groups using carbodiimide conjugation reactions (e.g., 1-ethyl-3(3-dimethylamino propyl)carbodiimide (EDC)); primary amines can be reacted with other amine groups using glutaraldehyde; CNBr treatment can convert hydroxyl groups to cyanate ester or imidocarbonate groups which can be reacted with primary amines; and cyanuric chloride treatment can convert primary amines to chlorotriazines which can be reacted with primary amines or thiols. For a review of useful conjugation reactions, see, e.g., Wong, ed., *Chemistry of Protein Coniugation and Cross-Linking*, CRC Press, Boca Raton, Fla. (1993).

Alternatively, adaptor molecules can include one member of an affinity binding pair and the receptor molecules can be conjugated to the other member of the binding pair such that the receptor molecules can be attached to the receptor area through the binding pair. Affinity binding pairs useful in this context include, without limitation, the biotin and streptavidin binding pair and the digoxigenin and antidigoxigenin binding pair. Thus, for example, and without limitation, adaptor molecules can be conjugated to avidin or streptavidin to cause immobilization of biotinylated receptor molecules. For antibody receptor molecules, the antibody itself can serve as an affinity binding partner with Protein A, which can be immobilized on the receptor area.

Patterns of receptor molecules, including blocking molecules, can be formed with or without adaptor molecules, using chemical printing or stamping methods, or photoreactive molecules using irradiative patterning with masks.

In some embodiments, the receptor molecules, including blocking molecules, are attached to the receptor area using self-assembled monolayers (SAMs). SAMs are formed by a particular form of adaptor molecule in the central portion of each molecule (i.e., the portion between the alpha and omega groups) interacts with the central portion of neighboring molecules in the monolayer to form a relatively ordered array. SAMs have been formed on a variety of surfaces or substrates including, but not limited to, silicon dioxide, gallium arsenide and gold. SAMs are applied to surfaces in predetermined patterns by a variety of techniques well known in the art, including simple flooding of a surface and more sophisticated methods such as microstamping and irradiative patterning. Monolayers may be produced with varying characteristics and with various omega reactive groups at the free end of the molecules which form the SAM. Therefore, by conjugating various receptor molecules to the SAMs through the omega reactive groups, SAMs with very specific binding affinities can be produced. This also allows for the production of patterned SAMs in which a plurality of receptor sites can differ from each other in the specific receptor molecules presented, and/or blocking sites can be interspersed with receptor sites.

For example, U.S. Pat. No. 5,512,131, incorporated herein by reference, discloses methods for the formation of microstamped patterns of SAMs on surfaces. In accordance with these methods, SAM patterns can be applied to the receptor area using a stamp in a "printing" process in which the "ink" consists of a solution including a compound capable of chemisorbing to form a SAM. The ink is applied to the surface using the stamp and deposits a SAM on the surface in a pattern determined by the pattern on the stamp. The surface may be stamped repeatedly with the same or different stamps in various orientations and with the same or different SAM-forming solutions. In addition, after stamping, the portions of the surface which remain bare or uncovered by a SAM may be derivatized with blocking molecules. Thus, for example, a grid pattern may be created in which the square regions of the grid bind different molecules or pathogens of interest but the linear regions of the grid bind different cells or molecules of interest. See, U.S. Pat. No. 6,368,838, incorporated herein by reference.

A wide variety of surface materials and SAM-forming compounds are suitable for use in the present invention. Useful combinations of surface materials and alpha reactive groups include, without limitation, metals such as gold, silver, copper, cadmium, zinc, palladium, platinum, mercury, lead, iron, chromium, manganese, tungsten, and any alloys of the above when employed with sulfur-containing alpha reactive groups such as thiols, sulfides, disulfides, and the like; doped or undoped silicon employed with silanes and chlorosilanes; metal oxides such as silica, alumina, quartz, glass, and the like employed with carboxylic acids; platinum and palladium employed with nitrites and isonitriles; and copper employed with hydroxamic acids. Additional suitable alpha reactive groups include acid chlorides, anhydrides, sulfonyl groups, phosphoryl groups, hydroxyl groups and amino acid groups. Additional surface materials include germanium, gallium, arsenic, and gallium arsenide. Additionally, epoxy compounds, polysulfone compounds, plastics and other polymers may find use as the surface material in the present invention. Polymers used to form bioerodable articles, including but not limited to polyanhydrides, and polylactic and polyglycolic acids, are also suitable. Additional materials and functional groups suitable for use in the present invention can be found in U.S. Pat. No. 5,079,600, incorporated herein by reference.

The central portion of the molecules comprising the SAM-forming compound may include a spacer functionality connecting the alpha reactive group and the omega reactive group. Alternatively, the spacer may essentially comprise the omega group, if no particular reactive group is required (e.g., for blocking molecules). Any spacer that does not disrupt SAM packing and that allows the SAM layer to be somewhat impermeable to organic or aqueous environments is suitable. The spacer may be polar, non-polar, halogenated (e.g., fluorinated), positively charged, negatively charged, or uncharged. For example, a saturated or unsaturated, linear or branched alkyl, aryl, or other hydrocarbon spacer may be used.

In one nonlimiting embodiment, the receptor area of a resonant sensor is coated with gold and alkyl-thiol SAMs are bound to the gold surface. Because the degree of ordering improves as the grain size of the gold film increases, vacuum deposition processes such as electron beam evaporation can be used to produce oriented surfaces with grain sizes on the order of tens of nanometers. The alkyl chain length of the SAM layer is chosen to be approximately 1–50 units (e.g., 10, 20, 30 or 40 units), which represents a balance between the degree of ordering of the layer and the cost of synthesis. Different SAMs with different omega groups are patterned onto the surface to form arrays of receptor sites. The reactive groups of the receptor molecules are then reacted with the omega groups of the SAMs to form the completed receptor areas. The surfaces of the resonant sensor that are distinct from receptor area (i.e., the silicon microstructure) can also be treated, for example, to prevent non-specific binding. For example, a PEO-terminated SAM layer that has a siloxane group for attachment to the silicon surface can be used to prevent non-specific binding to the silicon microstructure.

To attach receptor molecules to the SAM, standard activation-binding-inactivation protocols are used. For example, carboxyl-terminated SAM molecules can be activated by soaking the sensor surface in a solution of EDC (e.g., 0.01–0.05M) and N-hydroxysuccinimide (NHS) (e.g., 0.04–0.20M) in deionized water or buffer at pH 4–7 for 30 minutes. Next, a buffer solution (e.g., phosphate buffered saline (PBS)) containing the receptor molecules, at, e.g., about 0.1 µg/ml to 250 µg/ml, can be spotted onto the sensor surface using a nanoliter dispensing system to deliver a volume sufficient to cover the sensor surface (e.g., several nanoliters). Coupling can proceed for a period of 1–2 hours in a humidity-controlled environment to minimize the effects of evaporation. The sensor surface can then be washed with PBS, to remove adsorbed material that is not covalently bonded. Finally, the sensor surface can be immersed in an inactivation solution of sodium phosphate to quench any unreacted carboxyl groups. This process takes about 20 minutes. The sensor then can be washed and stored in PBS, or a different protocol can be employed to react different receptors molecules to different omega groups attached to different receptor sites.

Equivalents

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A sensor chip including a substrate, a plurality of anchors, a plurality of tethers, and a moving member coupled to the substrate and disposed for movement relative to the substrate, wherein the anchors are fixed relative to the substrate and the tethers are connected to the anchors and the moving member, the moving member having an oscillatory motion in a first direction and an oscillatory motion in a second direction in response to movement of the substrate, the first direction being different than the second direction, the moving member including a plurality of receptors, the receptors being configured for selectively binding to a first measurand.

2. A sensor chip according to claim 1, the sensor chip including a plurality of moving members, each of the moving members being coupled to the substrate for movement relative to the substrate, each of the moving members including a plurality of receptors, the receptors of each moving member being configured for selectively binding to a measurand.

3. A sensor chip according to claim 2, the receptors of a first moving member being configured for selectively binding to a first measurand and the receptors of a second moving member being configured for selectively binding to a second measurand, the first measurand being different than the second measurand.

4. A sensor chip according to claim 2, the receptors of a first moving member being configured for selectively binding to a first measurand and the receptors of a second moving member being configured for selectively binding to a second measurand, the receptors of the first moving member being different than the receptors of the second moving member, the first measurand being the same as the second measurand.

5. A sensor chip according to claim 1, the moving member, the tethers, and the anchors comprising silicon.

6. A sensor chip according to claim 1, the moving member comprising metal.

7. A sensor chip according to claim 6, the metal being a member of the group consisting of nickel, iron, gold, and copper.

8. A sensor chip according to claim 1, the moving member defining a first plane, the substrate defining a second plane, the first plane being substantially parallel to the second plane.

9. A sensor chip according to claim 8, the first direction and the second direction being substantially parallel to the first plane, the first direction being substantially perpendicular to the second direction.

10. A sensor chip according to claim 9, the moving member also oscillating relative to the substrate about an axis substantially perpendicular to the first plane in response to movement of the substrate.

11. A sensor chip according to claim 1, further including an optical grating disposed on the moving member and an optical grating disposed on the substrate, the optical gratings permitting measurement of the position of the moving member relative to the substrate in the first and second directions.

12. A sensor chip according to claim 1, the first direction being substantially perpendicular to the second direction.

13. A sensor chip according to claim 1, the first direction being substantially linear, the second direction being rotational.

14. A method of determining a property of a sample, comprising:
   A. providing a sensing chip, the sensing chip including a substrate, a plurality of anchors, a plurality of tethers, and a resonant sensor, the resonant sensor including a moving member disposed for movement relative to the substrate, wherein the anchors are fixed reletive to the substrate and the tethers are connected to the anchors and the moving member;
   B. exposing the sensing chip to a sample;
   C. moving the substrate;
   D. monitoring an oscillatory movement, relative to the substrate, of the moving member in a first direction; and
   E. monitoring an oscillatory movement, relative to the substrate, of the moving member in a second direction, the second direction being different than the first direction.

15. A method according to claim 14, the property of the sample being whether the sample includes a particular measurand.

16. A method according to claim 15, the measurand being an analyte.

17. A method according to claim 14, further including comparing monitored movements of the moving member in the first and second direction with predetermined functions.

18. A method according to claim 17, the predetermined functions representing previously monitored movements of the moving member relative to the substrate.

19. A method according to claim 14, further including comparing monitored movements of the moving member in the first and second directions with previously monitored movements of the moving member in the first and second directions.

20. A method according to claim 14, further including monitoring a magnitude and phase of a frequency response of the moving member.

21. A method according to claim 20, further including comparing the monitored magnitude and phase of the frequency response with predetermined functions.

22. A method of determining a property of a sample, comprising:
   A. providing a first sensing chip, the first sensing chip including a first substrate, a pluarlity of anchors, a plurality of tethers, and a first resonant sensor, the first resonant sensor including a first moving member disposed for movement relative to the first substrate, wherein the anchors are fixed relative to the substrate and the tethers are connected to the anchors and the moving member;
   B. measuring a response of the first moving member to a first environment, including the steps of:
      1. exposing the first sensing chip to a first environment;
      2. moving the first substrate;
      3. monitoring an oscillatory movement of the first moving member in a first direction; and;
      4. monitoring an oscillatory movement of the first moving member in a second direction, the second direction being different than the first direction;
   C. providing a second sensing chip, the second sensing chip including a second substrate, a plurality of anchors, a plurality of tethers, and a second resonant sensor, the second resonant sensor including a second moving member disposed for movement relative to the second substrate, wherein the anchors are fixed relative to the substrate and the tethers are connected to the anchors and the moving member;
   D. measuring a response of the second moving member to a second environment, the second environment being different than the first environment, including the steps of:
      1. exposing the second sensing chip to a second environment;
      2. moving the second substrate;
      3. monitoring an oscillatory movement of the second moving member in the first direction; and;
      4. monitoring an oscillatory movement of the moving member in the second direction;
   E. comparing the measured responses of the first and second moving members.

23. A method according to claim 22, wherein exposing the second sensing chip to a second environment comprises exposing the second resonant sensor to a sample.

24. A method of determining a property of a sample, comprising:
   A. providing a sensing chip, the sensing chip including a substrate, a plurality of anchors, a plurality of tethers, and a resonant sensor, the resonant sensor including a moving member disposed for movement relative to the substrate, wherein the anchors are fixed relative to the substrate and the tethers are connected to the anchors and the moving member;
   B. measuring a response of the moving member to a first environment, including the steps of:
      1. exposing the sensing chip to a first environment;
      2. moving the substrate;
      3. monitoring an oscillatory movement of the moving member in a first direction; and;
      4. monitoring an oscillatory movement of the moving member in a second direction, the second direction being different than the first direction;
   C. measuring a response of the moving member to a second environment, the second environment being different than the first environment, including the steps of:
      1. exposing the sensing chip to a second environment;
      2. moving the substrate;
      3. monitoring an oscillatory movement of the moving member in the first direction; and;
      4. monitoring an oscillatory movement of the moving member in the second direction;
   D. comparing the measured responses of the moving member in response to the first and second environments.

25. A sensing system comprising:
   A. a sensor chip, the sensor chip including a substrate and a moving member coupled to the substrate and disposed for movement relative to the substrate, the moving member moving in an oscillatory manner relative to the substrate in a first direction and in an oscillatory manner in a second direction in response to movement of the substrate, the first direction being different than the second direction;
   B. an optical system, the optical system generating an output signal representative of movement of the moving member in the first direction and of movement of the moving member in the second direction.

26. A system according to claim 25, the first direction being substantially perpendicular to the second direction.

27. A system according to claim 25, the first direction being substantially linear, the second direction being rotational.

28. A system according to claim 25, the moving member defining an optical grating, the substrate defining an optical grating, the optical system monitoring light diffracted from the optical gratings.

29. A system according to claim 25, the sensor chip including a plurality of moving members, each of the moving members being disposed for movement relative to the substrate in a first direction and a second direction.

30. A system according to claim 29, further including a cover for isolating one or more of the moving members from an ambient environment.

31. A system according to claim 29, a first one of the moving members including a first receptor area, a second one of the moving members including a second receptor area.

32. A system according to claim 31, the first receptor area and the second receptor area being configured for selectively binding to a first measurand.

33. A system according to claim 31, the first receptor area being configured for selectively binding to a first measurand, the second receptor area being configured for selectively binding to a second measurand.

34. A system according to claim 33, the first measurand being different than the second measurand.

35. A system according to claim 33, the receptors of the first receptor area being different than the receptors of the second receptor area, the first measurand being the same as the second measurand.

36. A system according to claim 25, the moving member including a plurality of receptors, the receptors being configured for selectively binding to a first measurand.

37. A sensing system comprising:
   A. a sensing chip, the sensing chip including a substrate and a resonant sensor, the resonant sensor including a moving member and a connector, the connector coupling the moving member to the substrate, the moving member being disposed for movement relative to the substrate, the moving member oscillating, relative to the substrate, in a first direction and oscillating, relative to the substrate, in a second direction in response to movement of the substrate;
   B. an optical system, the optical system generating an output signal representative of a frequency of oscillation of the moving member in the first direction and of a frequency of oscillation of the moving member in the second direction.

38. A sensing system comprising:
   A. a sensing chip, the sensing chip including a substrate and a plurality of resonant sensors, each of the resonant sensors including a moving member disposed for movement relative to the substrate, the moving member of each of the sensors oscillating, relative to the substrate, in a first direction and oscillating, relative to the substrate, in a second direction in response to movement of the substrate;
   B. an optical system, the optical system generating an output signal representative of a frequency of oscillation of each of the moving members in the first direction and of a frequency of oscillation of each of the moving members in the second direction.

39. A sensor chip including a substrate and a moving member coupled to the substrate and disposed for movement relative to the substrate, the moving member having an oscillatory motion in a first direction and an oscillatory motion in a second direction in response to movement of the substrate, the first direction being different than the second direction, the moving member including a plurality of receptors, the receptors being configured for selectively binding to a first measurand, wherein the sensor chip also includes an optical grating disposed on the moving member and an optical grating disposed on the substrate, the optical gratings permitting measurement of the position of the moving member relative to the substrate in the first and second directions.

40. A method of determining a property of a sample, comprising:
   A. providing a sensing chip, the sensing chip including a substrate and a resonant sensor, the resonant sensor including a moving member disposed for movement relative to the substrate, wherein the sensing chip also includes an optical grating disposed on the moving member and an optical grating disposed on the substrate;
   B. exposing the sensing chip to a sample;
   C. moving the substrate;
   D. monitoring an oscillatory movement with the optical gratings, relative to the substrate, of the moving member in a first direction; and
   E. monitoring an oscillatory movement with the optical gratings, relative to the substrate, of the moving member in a second direction, the second direction being different than the first direction.

* * * * *

UNITED STATES PATENT AND TRADEMARK OFFICE
CERTIFICATE OF CORRECTION

PATENT NO. : 7,178,378 B2  
APPLICATION NO. : 10/651338  
DATED : February 20, 2007  
INVENTOR(S) : Crawley et al.

Page 1 of 1

It is certified that error appears in the above-identified patent and that said Letters Patent is hereby corrected as shown below:

Column 29, line 15, please replace "reletive" with -- relative --

Column 29, line 52, please replace "pluarlity" with -- plurality --

Signed and Sealed this

First Day of May, 2007

JON W. DUDAS  
*Director of the United States Patent and Trademark Office*